United States Patent [19]

Miki et al.

[11] 4,182,866

[45] Jan. 8, 1980

[54] 3-HETEROCYCLIC SUBSTITUTED CEPHEM COMPOUNDS

[75] Inventors: Takuichi Miki, Amagasaki; Taisuke Matsuo, Ibaraki; Tohru Sugawara, Otsu; Hirotomo Masuya, Hyogo, all of Japan

[73] Assignee: Takeda Chemical Industries, Ltd., Osaka, Japan

[21] Appl. No.: 684,738

[22] Filed: May 10, 1976

[30] Foreign Application Priority Data

May 12, 1975 [GB] United Kingdom ............... 19912/75
Oct. 31, 1975 [GB] United Kingdom ............... 45236/75

[51] Int. Cl.² ......................................... C07D 501/20
[52] U.S. Cl. .................................... 544/27; 424/246; 544/16
[58] Field of Search ................ 260/243 C; 544/16, 27

[56] References Cited

U.S. PATENT DOCUMENTS

| | | | |
|---|---|---|---|
| 3,516,997 | 6/1970 | Takano et al. ................. | 260/243 C |
| 3,947,413 | 3/1976 | Christensen et al. .................. | 544/30 |
| 3,979,384 | 9/1976 | Firestone et al. ........................ | 544/27 |
| 3,997,528 | 12/1976 | Yoshioka et al. ........................ | 544/27 |
| 4,007,170 | 2/1977 | Berger et al. ..................... | 260/243 C |

OTHER PUBLICATIONS

Chemical Abstracts, vol. 82 31343m, Abstracting Ger. Offen. 2,415,402, dated 10-3-74.

*Primary Examiner*—Nicholas S. Rizzo
*Attorney, Agent, or Firm*—Wenderoth, Lind & Ponack

[57] ABSTRACT

Novel cephem compounds having a group of the formula at the 3-position thereof:

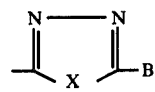

wherein X represents oxygen, sulfur or imino, which may be substituted; and B represents hydrogen or a hydroxyl, amino, mercapto or hydrocarbon group, which groups may be substituted, can be prepared by reacting a 3-formylcephem compound with a hydrazine compound of the formula:

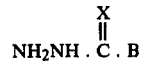

wherein the symbols have the same meanings as above, and subjecting the thus obtained compound to an oxidative ring-closure reaction. The objective compounds are found to have a broad antimicrobial spectrum and, in particular, are effective against gram-negative bacteria including *Escherichia Coli, Klebsiella pneumoniae, Proteus vulgaris, Proteus mirabilis, Proteus rettgerii,* as well as gram positive ones, and have low-toxity. Thus, these compounds may be used for antimicrobial agents in therapeutical purpose.

8 Claims, No Drawings

3-HETEROCYCLIC SUBSTITUTED CEPHEM COMPOUNDS

The present invention relates to novel antibiotics and to a process for producing them.

We have succeeded in synthesizing a novel type cephalosporin derivative; i.e. a cephem derivative whose cephem ring is combined directly with a heterocyclic ring at its 3-position, and we have found that the compounds of this type have strong antibiotic properties. This invention is the culmination of these findings.

The present invention is therefore directed to:

(1) a process for producing a cephalosporin compound (II) having a group of the formula:

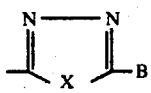

wherein X represents oxygen, sulfur or imino, which may be substituted; and B represents hydrogen or a hydroxyl, amino, mercapto or hydrocarbon group, which groups may be substituted;
which method comprises reacting a 3-formylcephem compound with a hydrazine compound of the formula:

wherein the symbols have the same meanings as above,
and subjecting the thus obtained compound to an oxidative ring-closure reaction;

(2) a process for producing a cephalosporin compound (II), which comprises (i) subjecting a cephem compound (III) having at its 3-position a hydrazone group of the formula;

wherein the symbols have the same meaning as above, to a oxidative ring-closure reaction; (ii) acylating an 7-aminocephem compound, i.e. a cephalosporin compound having at its 7-position an amino group and at its 3-position a group of the formula;

wherein the symbols have the same meanings as above.
(3) a cephem compound (III); and
(4) a cephalosporin compound (II).

By the 3-formylcephem compounds, the starting compounds of the present invention, is meant the cephalosporin compounds having a formyl group at the 3-position and which may be obtained, e.g., by oxidizing the corresponding 3-hydroxymethylcephem compounds (see Japanese patent publication No. Sho 46-20707, Japanese Pat. as laid-open No. Sho 47-933, ibid. 49-80097). The 3-formylcephem compounds comprise those represented by the formula

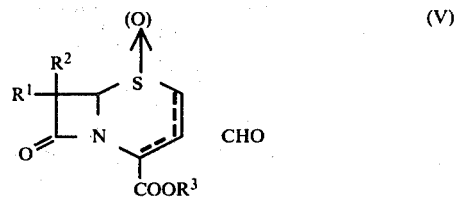

wherein R¹ represents an amino group, which may be protected, R² represents hydrogen or a lower alkoxy group, and —COOR³ refer to a carboxyl group which may be esterified. By the amino group which may be protected is meant an amino group or a protected amino group with a proton or an acyl group or a protecting group of the amino group as hereinafter illustrated. As the acyl group, there may be generally used carboxylic acid acyl groups which may be straight- or branched-chain, cyclic or a cyclic groups, and may contain unsaturated bonds or nitrogen, oxygen and/or sulfur in the groups. Especially, the acyl group may be for instance one of the acyl groups found in the corresponding moieties of the 6-position of penicillins or the 7-position of cephalosporins, e.g. aliphatic carboxylic acid acyl groups such as formyl, acetyl, propionoyl, hexanoyl, butanoyl, heptanoyl, octanoyl, cyclopentanoyl, etc.; mono-substituted aliphatic carboxylic acid acyl groups such as cyclopropylacetyl, cyclobutylacetyl, phenylacetyl, thiazolylacetyl, thiadiazolylacetyl, isoxazolylacetyl, 2-thienylacetyl, tetrazolylthioacetyl, tetrazolylacetyl, 1-cyclohexenylacetyl, cyclohexadienylacetyl, cyanoacetyl, phenoxyacetyl, acetoacetyl, ω-halogenoacetoacetyl, 4-methylthio-3-oxobutyryl, 4-carbamoylmethylthio-3-oxobutyryl, α-phenoxypropionyl, α-phenoxybutyroyl, p-nitrophenylacetyl, α-(2-pyridyloxy)-acetyl, α-(3-pyridyloxy)-acetyl, α-(4-pyridyloxy)-acetyl, 2-(2-hydroxythiazol-4-yl)-acetyl, 2-(2-iminothiazolin-4-yl)-acetyl, 4-pyridylthioacetyl, 2-(3-sydnone)-acetyl, 1-pyrazolylacetyl, 2-furylacetyl, 6-(2'-oxo-3'-methyl-pyradizinyl)-thioacetyl, etc.; di-substituted aliphatic carboxylic acid acyl groups such as α-carboxylphenylacetyl, α-aminophenylacetyl, mandelyl, α-sulfophenylacetyl, α-sulfo-(p-aminophenyl)-acetyl, phenylglycyl, 1-cyclohexenylglycyl, 1,4-cyclohexadienylglycyl, thienylglycyl, furylglycyl, cyclohexadienylglycyl, α-(β-methylsulfonylethoxycarbonyl)-phenylacetyl, 5-amino-5-carboxybutyryl, etc.; aromatic acyl groups such as benzoyl, p-nitro-benzoyl, etc.; heterocyclic acyl groups such as 5-methyl-3-phenyl-4-isooxazolylcarbonyl or 3-(2,6-dichlorophenyl)-5-methyl-4-isooxazolylcarbonyl.

When such acyl groups have such a functional group or groups as amino or carboxyl, these groups may be protected by the conventional protecting groups therefor. The protecting groups of an amino group may be exemplified by, e.g., aromatic acyl groups such as phthaloyl, benzoyl, p-nitrobenzoyl, toluoyl, naphthoyl, p-tert-butylbenzoyl, p-tert-butylbenzenesulfonyl, phenylacetyl, benzenesulfonyl, phenoxyacetyl, toluenesulfonyl, chlorobenzoyl, etc.; aliphatic acyl groups such as acetyl, valeryl, capryryl, n-decanoyl, acryloyl, pivaloyl, camphorsulfonyl, methanesulfonyl, chloroacetyl, etc.; esterified carboxyl groups such as ethoxycarbonyl, isobornyloxycarbonyl, phenyloxycarbonyl, trichloroethoxycarbonyl, benzyloxycarbonyl, etc.; carbamoyl groups such as methylcarbamoyl, phenylcarbamoyl, naphthylcarbamoyl, etc.; or the corresponding thiocarbamoyl groups, etc. The protecting groups of the carboxyl group may be exemplified by, e.g., methyl, ethyl, tert-butyl, tert-amyl, benzyl, p-nitrobenzyl, p-methoxybenzyl, benzhydryl, 1-indanyl, phenacyl, phenyl, p-nitrophenyl, methodymethyl, ethoxymethyl, benzyloxymethyl, acetoxymethyl, pivaloyloxymethyl, β-methylsulfonylethyl, methylthiomethyl, trityl, β,β,β-trichloroethyl or silyl (e.g. trimethylsilyl, dimethylsilyl, etc.).

Thus, the acyl groups may comprise groups represented by the formula:

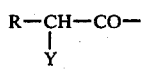

wherein R is an alkyl, aralkyl, aryl, halogenoacetyl or hetero-ring group, or a group having as a substituent any of the above groups through oxygen or sulfur, and these groups may be further substituted for example with a halogen, nitro, amino, hydroxy, carboxamido, alkyl, alkoxyl, alkythio, guanidino, guanidinomethyl or carboxymethyl group and; Y is hydrogen, hydroxy, or amino, sulfo or carboxyl, which may be esterified or amidified. Preferable acyl groups may be represented by the formula:

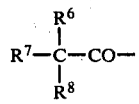

wherein $R^6$ represents 2-thienyl, phenyl, p-hydroxyphenyl, or 2-iminothiazolin-4-yl group, $R^7$ represents hydrogen or hydroxyl or amino group, $R^8$ represents hydrogen, or $R^7$ and $R^8$ represents jointly methoxyimino group.

The lower alkoxy group represented by $R^2$ may be exemplified by methoxy, ethoxy, etc. By the carboxyl group which may be esterified (—COOR$^3$) is meant a carboxyl group or its inorganic or organic salt with, for example, an alkali or alkaline-earth metal (e.g. sodium, potassium, etc.), triethylamine etc. or carboxyl group esterified with e.g. an α-acyloxy-α-substituted methyl group such as benzyl, p-nitrobenzyl, di-or tri-alkylsilyl, alkoxysilyl, benzhydryl, alkoxyalkyl, alkenyl, trichloroethyl, methylsulfonylethyl, benzoylmethyl, t-butyl, methoxybenzyl, trityl, methylthiomethyl, pivaloyloxymethyl, α-acetoxybutyl, etc. The esterified carboxyl groups are desired to be convertible to free carboxyl groups by such mild conditions as do not affect the β-lactam ring, etc. Preferred esterified groups have a group represented by $R^3$ which may be converted to hydrogen by mild acidic or alkaline conditions, and such a group is exemplified by diphenylmethyl, p-nitrobenzyl, a substituted phenyl, a lower alkylsulfonylethyl, pivaloyloxymethyl, etc. Other preferred such esterified carboxyl groups have a group $R^3$ which may be removed by oxidation or reduction, e.g. trichloroethyl, benzyl, etc. Such a group as —COOR$^3$ is

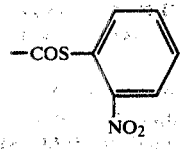

etc., which may be easily converted to a free carboxyl group by hydrogenation, is also included amongst preferred options.

In the hydrazine compounds (I), another starting material, the substituent of the "imino group which may be substituted" represented by X, is exemplified by a lower alkyl group such as methyl, ethyl, etc. or a lower alkyl group substituted by hydroxy, mercapto, amino, morpholino, carboxyl, sulfo, carbamoyl, an alkoxycarbonyl, an alkoxyl, an alkylthio, an alkylsulfonyl, an acyloxy or a morpholinocarbonyl group.

The substituent of hydroxy, amino, mercapto, carbamoyl or a hydrocarbon group (e.g. an alkyl group such as methyl, ethyl, propyl, iso-butyl, tert-butyl, etc., and aralkyl group such as benzyl, etc., an aryl group such as phenyl, naphtyl, etc.) may be exemplified by, e.g., a lower alkyl group as mentioned above, an acyl group such as acetyl, propionyl, etc., an aralkyl group such as benzyl, etc., or an aryl group such as phenyl, etc. Preferable groups represented by the symbol B are acetylamino, dimethylamino and N-acetyl-N-methylamino group.

In the reaction of the present invention, a 3-formyl compound and a hydrazine compound (I) are firstly reacted with each other. The reaction is an equimolar reaction, but, generally, it is desirable to employ a slight excess of the hydrazine compound (I). The reaction is usually and desirably conducted in a solvent e.g. ethers such as dimethylsulfoxide, dimethylformamide, dioxane, tetrahydrofuran, diethylether, etc., alcohols such as methanol, ethanol, butanol, isopropanol, etc., esters such as ethyl acetate, ethyl formate, etc., other organic solvents such as benzene, toluene, chloroform, etc., or a mixture thereof. It is preferable to allow the reaction to proceed under such mild conditions as below 80° C., and the reaction is usually completed within 5 hours. The cephem compounds (III) show good crystallization properties and may be purified by a per se known purification method such as an ion-exchange method, a chromatographic technique, etc. The cehpem compounds (III) may be subjected to the next reaction by using the reaction mixture as it is.

The thus obtained cephem compounds (III) are subjected to an oxidative ring-closure reaction. In this reaction, there may be used generally such oxidizing agents as act under mild conditions, which are exemplified by e.g. dichlorodicyanobenzoquinone, chloranil, manganese dioxide, ferric chloride, N-chloro or bromosuccinimide, N-chloro or bromosulfonamide, hydrogen peroxide, acetyl hydroperoxide, lead tetraacetate, diethyl azodicarboxylate, etc. Preferable oxidizing agents (e.g. dichlorodicyanobenzoquinone, chloranil, etc.) are those acting under neutral or weakly acidic condition, principally on the compounds (III) by removing hydrogen therefrom. The reaction proceeds smoothly in the solvent in general, and the preferred solvents are ethers such as dioxane, diethylether, etc., dimethylsulfoxide, dimethylformamide, acetonitrile, nitromethane, etc. The reaction is desired to proceed at a temperature lower than 100° C., and is usually completed within 5 hours. The oxidative ring-closure reaction proceeds also by employing on electrooxidation technique. When the sulfur in the cephem ring is oxidized to form S-oxide by the oxidative ring-closure reaction, the oxide may be reduced to a non-oxide form by a per se known method employing tri-valent phosphorus compounds such as phosphorus trichloride, phosphorus tribromide, etc., di-valent tin or iron compounds, etc. For the purpose of increasing the solubility of the cephem compounds (II), and to accelerate the oxidative ring-closure reaction, the cephem compounds (III) may be converted, before the reaction, to their esters such as trimethylsilyl-, dimethylisobutylsilyl-, dimethylsilenyl-, dimethoxymethylsilyl, dibutylin-esters, etc. or to their acylated derivatives. By the preliminary modification of the cephem compounds (III), the yield of the cephalosporin compounds (II) increases in most cases. When a cephem-thiosemicarbazone of the formula (III)

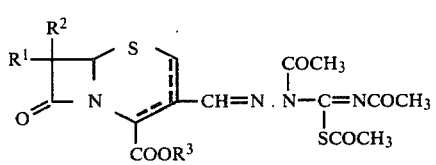

(III)

is, for example, subjected to the oxidative ring-closure reaction, the corresponding cephalosporin compounds (III, X=S, B=NHCOCH$_3$) is obtained in quantitative manner. Thus, when the preliminary modification is employed before the ring-closure reaction, the substituents (B, X, R$^{1-3}$, etc.) of the cephem compounds (III) are not limited to the case that they are the same as those of the cephalosporin compounds (II).

The acylation of a 7-aminocephem compound may be carried out by a similar manner as described in West Germany patent application as laid-open No. 2,461,478.

The resulting cephalosporin compounds (II) have strong antimicrobial properties and they are used as they are, or, if desired, after removal of the protecting groups such as the acyl group, etc., after the removal of the acyl groups, etc. attached to the group represented by the symbol B, or after conversion to their free form or to the corresponding organic or inorganic salts, as remedies against many diseases including tuberculosis. The cephalosporin compounds (II) may be used in the form of a pharmaceutically acceptable salt with a non toxic cation such as sodium, potassium or the like; a basic amino acid such as arginine, ornithine, lysine, histidine or the like; or a polyhydroxyalkylamine such as N-methylglucamine, diethanolamine, triethanolamine, trishydroxymethylaminomethane or the like. The compound (II) may also be used after it has been converted to a biologically active ester derivative by esterification of its 4-carboxyl group, said ester derivatives being conductive to, for instance, an increased blood level or/and a longer duration of activity or/and an increased absorption from the intestines, etc. As the ester residues of use for this purpose, there may be mentioned, for example, alkoxylmethyl and α-alkoxyethyl and other α-alkoxy-α-substituted methyl groups, e.g. methoxymethyl, ethoxymethyl, isopropoxymethyl, α-methoxyethyl, α-ethoxyethyl, etc.; alkylthiomethyl groups, e.g. methylthiomethyl, ethylthiomethyl, isopropylthiomethyl, etc.; and acyloxymethyl and α-acyloxy-α-substituted methyl groups, e.g. pivaloyloxymethyl, α-acetoxybutyl, etc.

The cephalosporin compounds (II) have a broad and potent antimicrobial spectrum, showing activity against gram-negative and gram-positive bacteria, and especially against such gram-negative bacteria as *Escherichia coli, Klebsiella pneumoniae, Proteus vulgaris, Proteus mirabilis* and *Proteus rettegerii*, these compounds (II) being more potent than the hitherto-known cephalosporins, while the compounds (II) are lower in toxicity against e.g. kidney than known cephalosporins (e.g. cefazolin). Thus, these compounds yield excellent therapeutic effects in the treatment of infections with these bacteria in human beings and animals.

Like the known cephalosporins, the contemplated compounds (II) of this invention can each be administered orally, or parenterally in various solid and liquid forms e.g. as powders, solutions, suspensions, etc., alone or in admixture with a physiologically acceptable vehicle or excipient in accordance with established pharmaceutical procedures.

Specifically, in the treatment of various human diseases caused by the above-mentioned bacteria, the contemplated compounds of this invention, such as sodium 3-(5-amino-1,3,4-thiadiazol-2-yl)-7-thienylacetamido-3-cephem-4-carboxylic acid, sodium 3-(5-acetylamino-1,3,4-thiadiazol-2-yl)-7-(2-thienylacetamido)-3-cephem-4-carboxylic acid, sodium 3-(5-acetamino-1,3,4-thiadiazol-2-yl)-7-(2-thiazolylacetamido)-3-cephem-4-carboxylic acid, sodium 3-(5-acetamino-1,3,4-thiadiazol-2-yl)-7-(4-pyridylthioacetamido)-3-cephem-4-carboxylic acid, 3-(5-acetamido-1,3,4-thiadiazol-2-yl)-7-(2-iminothiazolin-4-yl)acetamido -3-cephem-4-carboxylic acid, 3-(5-acetamino-1,3,4-thiadiazol-2-yl)-7-(phenylglycylamino)-3-cephem-4-carboxylic acid, 3-(5-acetamino-1,3,4-thiadiazol-2-yl)-7-(4-hydroxyphenylglycylamino)-3-cephem-4-carboxylic acid, 3-(5-acetamino-1,3,4-thiadiazol-2-yl)-7-(cyclopropylglycylamino)-3-cephem-4-carboxylic acid, 3-(5-acetamido-1,3,4-thiadiazol-2-yl)-7-(cyclobutylglycylamino)-3-cephem-4-carboxylic acid, 3-(5-acetamido-1,3,5-thiadiazol-2-yl)-7-(cyclohexen-1-ylglycylamino)-3-cephem-4-carboxylic acid, 3-(5-amino-1,3,5-thiadiazol-2-yl)-7-(2-iminothiazoline-4-ylacetamido)-3-cephem-4-carboxylic acid, sodium 3-(5-methyl-1,3,4-thiadiazol-2-yl)-7-(2-thienylacetamido)-3-cephem-4-carboxylic acid, sodium 3-(5-methyl-1,3,4-thiadiazol-2-yl)-7-(2-iminothiazoline-4-ylacetamido)-3-cephem-4-carboxylic acid, 3-(5-methyl-1,3,4-thiadiazol-2-yl)-7-(4-hydroxyphenylglycylamino)-3-cephem-4-carboxylic acid, 3-(1,3,4-thiadiazol-2-yl)-7-(4-pyridylthioacetamido)-3-cephem-4-carboxylic acid, sodium 3-(1,3,4-thiadiazol-2-yl)-7-(2-iminothiazolin-4-ylacetamido)-3-cephem-4-carboxylic acid, 3-(1,3,4-thiadiazol-2-yl)-7-(phenylglycylamino)-3-cephem-4-carboxylic acid, 3-(1,3,4-thiadiazol-2-yl)-7-(4-hydroxyphenylglycylamino)-3-cephem-4-carboxylic acid, 3-(1,3,4-thiadiazol-2-yl)-7-(tetrazol-1-ylacetamido)-3-cephem-4-carboxylic acid, 3-(5-acetamido-1,3,4-triazol-2-yl)-7-(4-hydroxyphenylglycylamino)-3-cephem-4-carboxylic acid, 3-(5-acetamido-1,3,4-triazol-2-yl)-7-(2-iminothiazolin-4-ylacetamido)-3-cephem-4-carboxylic acid sodium salt, 3-(5-acetamido-1,3,4-oxadiazol-2-yl)-7-(4-hydroxyphenylglycylamino)-3-cephem-4-carboxylic acid, and 3-(5-acetylamido-1,3,4-thiadiazol-2-yl)-7-(2-(2-aminothiazol-4-yl)acetamido)-3-cephem-4-carboxylic acid, are each desirably administered parenterally (*non*-orally) at a daily dose level of about 5 to 20 mg./kg. body weight in 3 to 4 divided doses per day.

The invention is illustrated by the following examples:

EXAMPLE 1

To a solution of 0.915 g of methyl 3-formyl-7-thienylacetamido-3-cephem-4-carboxylate in 11 ml of dimethylsulfoxide is added 0.25 g of thiosemicarbazide. The mixture is stirred for 3 hours, poured into cold water and shaken with ethyl acetate. The organic layer is washed with a saturated aqueous solution of sodium chloride, dried over sodium sulfate, and the solvent is removed to give 0.97 g of the corresponding thiosemicarbazone as colourless needles. Melting Point: 202°–204° C.

IR: $\nu_{max}^{nujol}$ cm$^{-1}$: 1780($\beta$-lactam), 1720(ester), 1660(amide).

UV: $\lambda_{max}^{EtOH}$ nm($\epsilon$): 238(13,200), 348(27,500).

NMR(DMSO-d$_6$, ppm):

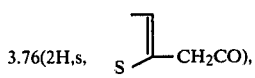 3.76(2H,s, 3.82(3H,s,—COOCH$_3$). 5.19(1H,d,C$_6$—H), 5.75(1H,q,C$_7$—H,

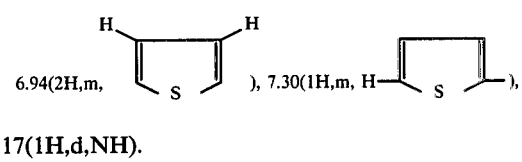 6.94(2H,m, ), 7.30(1H,m, 9.17(1H,d,NH).

EXAMPLE 2

To a solution of 0.5 g of the thiosemicarbazone obtained by the method of Ex. 1 in 10 ml of dimethylacetamide are added 10 ml of acetic anhydride. The mixture is stirred for 18 hours at 55° C., diluted with water and shaken with ethyl acetate. The organic layer is washed with a saturated aqueous solution of sodium chloride, dried over sodium sulfate and the solvent is evaporated. The residue is chromatographed on a column of silica gel and developed with ethyl acetate-benzene (3:2) to give 0.48 g of diacetate of the corresponding thiosemicarbazone as pale yellow crystals.

IR: $\nu_{max}^{KBr}$ cm$^{-1}$: 1780($\beta$-lactam), 1718(COOCH$_3$), 1660(CONH), 1605(double bond).

NMR(DMSO-d$_6$, ppm): 2.04(3H,s,SCOCH$_3$), 2.19(3H,s,NCOCH$_3$), 3.38(2H,dd,C$_2$—H), 3.73(2H,s,

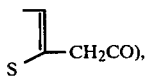

3.78(3H,s, COOCH$_3$), 5.12(1H,d,C$_6$—H), 5.58(1H,q,C$_7$—H),

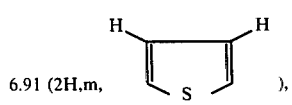 6.91 (2H,m, ),

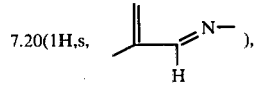 7.20(1H,s, ), 7.22 (1H,m, 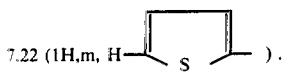 ).

EXAMPLE 3

The suspension of 0.3 g of the thiosemicarbazone obtained by the method of Ex. 1 in 3 ml of pyridine and 8 ml of acetic anhydride is stirred for 2 hours at room temperature to obtain a clear solution, which is poured into cold water and shaken with ethyl acetate. The extract is washed with a sodium bicarbonate solution, a dilute hydrochloric acid and a sodium chloride solution, successively, and dried over sodium sulfate, and the solvent is then evaporated. The residue is chromatographed on a column of silica gel and developed with ethyl acetatebenzene (1:1) to give 0.28 g of the corresponding triacetylthiosemicarbazone derivative.

IR: $\nu_{max}^{KBr}$ cm$^{-1}$: 1782($\beta$-lactam), 1730(COOCH$_3$), 1675(CONH).

NMR(DMSO-d$_6$, ppm); 2.18(3H,s,SCOCH$_3$), 2.37(6H,s,NCOCH), 3.73(3H,s,COOCH$_3$),

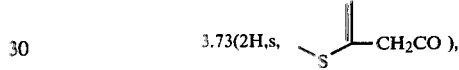 3.73(2H,s, 3.79 (2H,s,C$_2$—H), 5.11(1H,d,C$_6$—H), 5.78(1H,q,C$_7$—H),

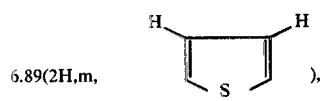 6.89(2H,m, ),

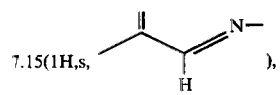 7.15(1H,s, ),

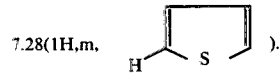 7.28(1H,m, ).

EXAMPLE 4

To a solution of 0.1 g of the triacetyl thiosemicarbazone in 5 ml of anhydrous dioxane is added 0.07 g of 2,3-dichloro-5,6-dicyanobenzoquinone (DDQ). The mixture is stirred for 7 hours at 100° C., and the solvent is evaporated in vacuo. The residue is chromatographed on silica gel and eluted with ethyl acetate-benzene (3:1) to give 0.078 g of methyl 3-(5-acetamido-1,3,4-thiadiazol-2-yl)-7-thienylacetamido-3-cephem-4-carboxylate as colourless needles.

Melting point: 237°–240° C.

Elemental analysis: Calcd. for C$_{18}$H$_{17}$N$_5$O$_5$S$_3$: C, 45.08; H, 3.57; N, 14.60; S, 20.06. Found: C, 45.06; H, 3.56; N, 14.46, S, 19.87.

IR: $\nu_{max}^{KBr}$ cm$^{-1}$: 1782($\beta$-lactam), 1736(COOCH$_3$), 1690(NHCOCH$_3$), 1650(NHCO).

NMR(DMSO-d$_6$, ppm): 2.18(3H,s,NHCOCH$_3$), 3.66(3H,s,COOCH$_3$), 3.74(2H,s, 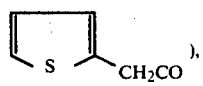), 3.99(2H,dd,C₂-H), 5.24(1H, d,C₆-H), 5.80(1H,q,C₇-H), 6.90(2H,m, 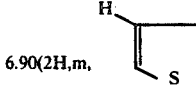), 7.30(1H,m,H— 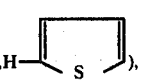), 9.2(1H,d,NH).

EXAMPLE 5

To a solution of 0.1 g of the diacetyl thiosemicarbazone in 5 ml of dry dioxane is added 0.07 g of 2,3-dichloro-5,6-dicyanobenzoquinone, and the mixture is stirred overnight at 45° C. The reaction mixture is treated by the procedure described in Ex.4 to obtain 0.08 g of methyl 3-(5-acetamido-1,3,4-thiadiazol-2-yl)-7-thienylacetamido-3-cephem-4-carboxylate.

EXAMPLE 6

To a stirred solution of 3.5 g of 3-formyl-7-thienylacetamido-3-cephem-4-carboxylic acid in 100 ml of tetrahydrofuran is added 2.3 g of diphenyldiazomethane, and the stirring is continued for 30 min. The solvent is distilled off under reduced pressure, and the residue is washed with petroleum ether to give 4.9 g of the corresponding 3-formyl-3-cephem-4-carboxylic acid benzhydryl ester.

IR: $\nu_{max}^{KBr}$ cm⁻¹: 1785(β-lactam),

1733(—COOCH  )₂,

1704(—CHO), 1650(CONH).

UV: $\lambda_{max}^{EtOH}$ nm(ε): 285(19,400).

NMR(DMSO-d₆, ppm): 3.41 and 3.91(1H×2 dd,C₂—H), 3.74(2H,s, 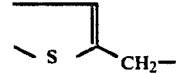), 5.25(1H,d,C₆—H), 5.90(1H,q,C₇—H), 7.03(1H,s,—CH(C₆H₅)₂), 7.2–7.5(10H, m,phenyl), 9.22 (1H,d,NH), 9.44(1H,s,—CHO).

EXAMPLE 7

A solution of 2.4 g of the 3-formyl cephem benzhydryl ester and 0.47 g of thiosemicarbazide in 6 ml of dimethylsulfoxide is stirred for 1 hour at 45° C., diluted with ice-water, and shaken with ethyl acetate. The ethyl acetate layer is washed with a sodium chloride solution, dried over sodium sulfate and concentrated in vacuo to give 2.6 g of the corresponding thiosemicarbazone.

IR: $\nu_{max}^{KBr}$ cm⁻¹: 1780(β-lactam), 1720(ester), 1663(amide).

UV: $\lambda_{max}^{EtOH}$ nm(ε): 350(27,800)

NMR(DMSO-d₆, ppm): 3.53, 4.52(2H, dd,C₂—H), 3.75(2H,s, 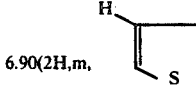), 5.19(1H,d,C₆—H), 5.79(1H,q,C₇—H), 6.9(2H,m, 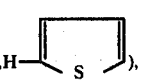), 7.2–7.5(11H,m,aromatic-H), 8.23(1H, 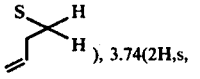 ), 9.17L (1H,d,NH).

EXAMPLE 8

A solution of 1.5 g of the thiosemicarbazone obtained in Example 7 in 30 ml of acetic anhydride and 15 ml of acetic acid is stirred at 50° C. for 20 hours. Excess acetic anhydride and acetic acid are distilled off under reduced pressure and the resulting product is a 1:1 mixture of diacetyl derivatives (A) and (B). The mixture is chromatographed on a column of silica gel and developed with dichloromethane-ethyl acetate (2:1). The first fraction gives 0.8 g of the compound (A) and the second fraction gives 0.6 g of the compound (B).

Compound (A)

IR $\gamma_{max}^{KBr}$ cm⁻¹: 1782(β-lactam), 1765(CH₃CO), 1705(ester), 1680(CONH).

UV $\lambda_{max}^{EtOH}$ nm(ε): 274(19,700).

NMR(DMSO-d₆ppm): 2.05(3H,s,SCOCH₃), 2.15(3H,s,NHCOCH₃), 3.42(2H,s, 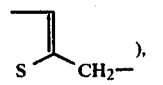 ), 3.74(2H,s, 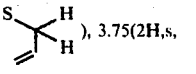), 5.15 1H,d,C₆—H J=4 Hz), 5.82(1H,q,C₇—H J=4, 9 Hz), 6.56

(1H,s, 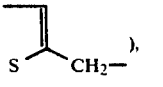 ), 6.94(1H,s,—CH—(C₆H₅)₂), 7.2–7.5 (10H, m, C₆H₅—), 9.23(1H,d,NH J=9 Hz).

Compound (B)

IR $\nu_{max}^{KBr}$ cm⁻¹: 1780(β-lactam).
UV $\lambda_{max}^{EtOH}$ nm (ε): 276(15,900).
NMR(DMSO-d₆, ppm): 2.02(3H,s,SCOCH₃), 2.18(3H,s,NHCOCH₃), 3.40(2H,q,  ), 3.75(2H,s,  ), 5.16 (1H,d,C₆—H J=5 Hz), 5.66(1H,q,C₇—H J=5, 9 Hz), 6.88 (1H,s,—CH(C₆H₅)₂), 7.2–7.6(10H,m,C₆H₅—), 9.16(1H,d,NH J=9 Hz), 11.79(1H,s,NH).

EXAMPLE 9

Two grams of 3-diacetylthiosemicarbazone derivative (1:1 mixture of the compounds (A) and (B)) obtained in Example 8 are dissolved in 30 ml of anhydrous dioxane and to the solution is added 1 g of DDQ, followed by stirring at 45° C. for 12 hours.

After cooling, the reaction mixture is filtered and the filter cake is washed with a small amount of dioxane. The combined filtrate is evaporated to dryness under reduced pressure and the residue is chromatographed on a column of silica gel (eluting with dichloromethane-ethylacetate (3:1)) to give 1.0 g of 3-(5-acetylamino-1,3,4-thiadiazol-2-yl)-7-thienylacetamido-3-cephem-4-carboxylic acid benzhydryl ester.

IR $\nu_{max}^{KBr}$ cm⁻¹: 1790(β-lactam), 1730(ester), 1695(NHCOCH₃), 1650(CONH).

UV $\lambda_{max}^{EtOH}$ nm(ε): 315(13,200). NMR(DMSO-d₆, ppm): 2.16(3H,s,NHCOCH₃),

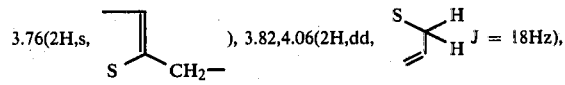

3.76(2H,s, ), 3.82,4.06(2H,dd, J = 18Hz), 5.25(1H,d,C₆—H J=4 Hz), 5.71(1H,q,C₇—H J=4, 8 Hz), 6.76(1H,s,COOCH), 6.9

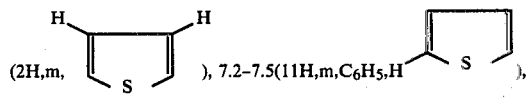

(2H,m, ), 7.2–7.5(11H,m,C₆H₅, 9.22(1H,d,NH J=8 Hz).

Elemental analysis Calcd. for C₃₀H₂₅N₅S₃O₅; C, 57.04; H, 3.99; N, 11.09; S, 15.23 Found: C, 56.80; H, 3.70; N, 10.83; S, 15.10.

EXAMPLE 10

30 mg of 3-thiadiazol-4-carboxylic acid benzhydrylester obtained in Example 9 are suspended in 1 ml of anisole, and to the mixture are added 3 ml of trifluoroacetic acid under stirring and ice-cooling. After 20 min., the solvent is distilled off under reduced pressure and the residue is triturated with ethyl acetate to precipitate 3-(5-acetylamino-1,3,4-thiadiazol-2-yl)-7-thienylacetamido-3-cephem-4-carboxylic acid. The product is filtered and washed with ether to give 18 mg of pale yellow crystals.

IR $\nu_{max}^{KBr}$ cm⁻¹: 1783(β-lactam), 1700(COOH), 1695(NHCOCH₃), 1660(CONH), 1610(double bond).

UV $\lambda_{max}^{EtOH}$ nm(ε): 254(14,100), 317(13,700).

NMR(DMSO-d₆, ppm): 1.98(3H,s,NHCOCH₃),

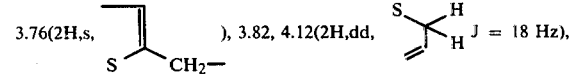

3.76(2H,s, ), 3.82, 4.12(2H,dd, J = 18 Hz), 5.22(1H,d,C₆—H J=4 Hz), 5.71(1H,q,C₇—H J=4, 8 Hz),

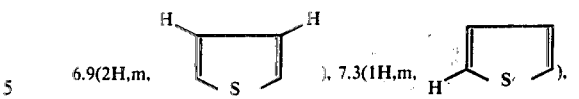

6.9(2H,m, ), 7.3(1H,m, ), 9.2(1H,d,NH J=8 Hz).

Sodium salt:

IR $\nu_{max}^{KBr}$ cm⁻¹: 1770(β-lactam), 1665(CONH), 1610(COO⁻).

NMR(D₂O, ppm): 2.47(3H,s,NHCOCH₃), 3.96, 4.20(2H,dd, J=18Hz),4.08(2H,s, ),

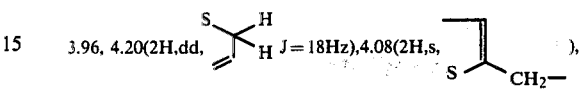

5.41 (1H,d,C₆—H J=5 Hz), 5.89(1H,d,C₇—H J=5 Hz),

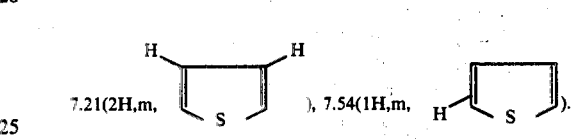

7.21(2H,m, ), 7.54(1H,m, ).

MIC (μg/ml).

| Organism | This product | Cephalothin |
|---|---|---|
| S. aureus 209p | ≦0.2 | 0.78 |
| E. coli NIHJ | 12.5 | 25 |
| P. vulgaris IFO 3988 | 0.78 | 3.13 |
| P. mirabilis | 1.56 | 3.13 |
| P. rettgeri | 6.25 | >100 |

EXAMPLE 11

To a solution of 1.2 g of 3-formyl-7-phenylacetamido-2-cephem-4-carboxylic acid in 10 ml of anhydrous dimethylsulfoxide is added 0.4 g of thiosemicarbazide, followed by stirring at room temperature overnight.

The reaction mixture is poured into ice-water and shaken with ethyl acetate. The organic layer is washed with a saturated aqueous solution of sodium chloride, and dried over anhydrous sodium sulfate. The solvent is evaporated and the residue is chromatographed on a column of silica gel (developing with benzene-acetone (3:1) to give 1.2 g of the hydrazone derivative, which is recrystallized from ethyl alcohol-water to afford colourless needles of the corresponding thiosemicarbazone.

Melting point: 167°–171° C.

IR $\nu_{max}^{KBr}$ cm⁻¹: 1740(β-lactam), 1725(COOH), 1662, 1655 (CONH, double bond).

NMR(DMSO-d₆, ppm): 3.58(2H,s,C₆H₅—CH₂—), 5.21(1H,d,C₆—H J=4 Hz), 5.44(1H,s,C₄—H), 5.50(1H,q,C₇—H J=4 8 Hz),

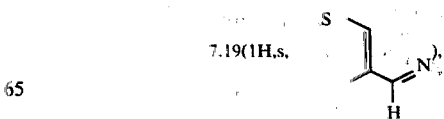

7.19(1H,s, ), 7.30(5H,s,C₆H₅—), 7.72(1H,s, 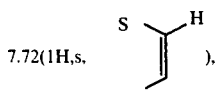 ), 7.4-8.2(3H, broad, NH), 9.13(1H,d,CONH J=8 Hz).

EXAMPLE 12

(1) A solution of diazomethane in ether is added to 1 g. of the thiosemicarbazone obtained in Example 11 dissolved in 15 ml of anhydrous tetrahydrofuran. After 30 min., the solvent is evaporated under reduced pressure and the residue is chromatographed on a column of silica gel (developing with benzene-acetone (3:1)) to give 0.8 g of the corresponding 4-carboxylic acid methyl ester as colourless columns.

Melting point: 215°-216° C.

IR $\nu_{max}^{KBr}$ cm$^{-1}$: 1775($\beta$-lactam), 1740(ester), 1670(CONH).

UV $\lambda_{max}^{EtOH}$ nm($\epsilon$): 323(42,900).

NMR(DMSO-d$_6$, ppm): 3.50(2H,s,C$_6$H$_5$CH$_2$—), 3.61(2H,s,COOCH$_3$), 5.12(1H,d,C$_6$—H J=4 Hz), 5.40(1H,q,C$_7$—H J=4, 8 Hz), 5.55(1H,s,C$_4$—H), 7.11(1H,s, 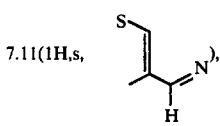 ), 7.2-7.3 (2H,broad, NH$_2$), 7.23(5H,s,C$_6$H$_5$), 8.07(1H,broad,NH), 9.13(1H,d,CONH J=8 Hz).

Elemental analysis: Calcd. for C$_{18}$H$_{19}$N$_5$S$_2$O$_4$ C, 49.88; H, 4.39; N, 16.17. Found: C, 49.99; H, 4.41; N, 16.02.

(2) A mixture of 4.04 g of 3-formyl-7-phenylacetamido-2-cephem-4-carboxylic acid methyl ester and 1.01 g of thiosemicarbazide in 20 ml of dimethyl sulfoxide is reacted at 45° C. The procedure gives 4.44 g (93%) of the corresponding 4-carboxylic acid methyl ester which is in good agreement with the product of the above method (1).

EXAMPLE 13

A mixture of 0.3 g of 3-thiosemicarbazone-2-cephem-4-carboxylic acid methyl ester obtained in Example 12, 1 ml of acetic anhydride and 0.5 ml of anhydrous pyridine is stirred at 40° C. for 1 hour. The solvent is distilled off under reduced pressure and to the residue is added 30 ml of ethyl acetate. The ethyl acetate layer is washed with a 5% sodium bicarbonate solution and then a saturated aqueous solution of sodium chloride, and dried over anhydrous sodium sulfate. After the removal of ethyl acetate, the resulting product is a (1:2) mixture of 3-(S,1,3-triacetylsemicarbazonomethyl)-7-phenylacetamido-2-cephem-4-carboxylic acid methyl ester and 3-(S,1-diacetylsemicarbazonomethyl)-2-cephem-4-carboxylic acid methyl ester. The mixture is chromatographed on a column of silica gel and developed with ethyl acetate-benzene (3:1). The procedure gives 0.12 g of the former, triacetyl derivative, and 0.21 g of the later, diacetyl derivative.

3-(S,1,3-triacetylsemicarbazonomethyl)-7-phenylacetamido-2-cephem-4-carboxylic acid methyl ester.

Melting point: 118°-119° C.(decomp.).

IR $\nu_{max}^{KBr}$ cm$^{-1}$: 1778($\beta$-lactam), 1740(ester).
UV $\lambda_{max}^{EtOH}$ nm ($\epsilon$): 260(14,300).
NMR(DMSO-d$_6$, ppm): 2.17(3H,s,SCOCH$_3$), 2.38(3H×2,s,NCOCH$_3$), 3.50(3H,s,C$_6$H$_5$—CH$_2$—), 3.67(3H,s,COOCH$_3$),

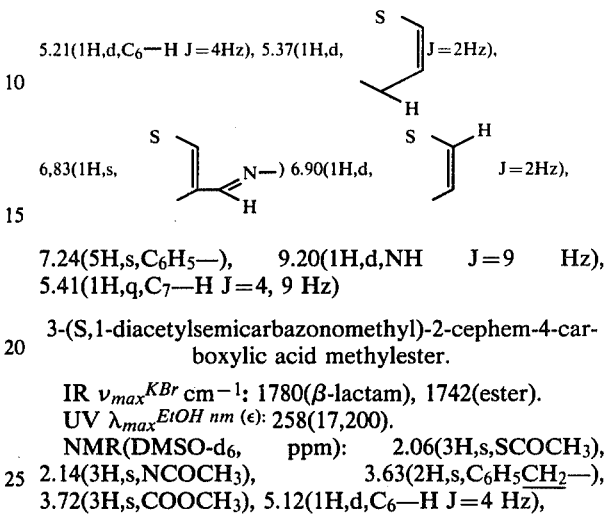

7.24(5H,s,C$_6$H$_5$—), 9.20(1H,d,NH J=9 Hz), 5.41(1H,q,C$_7$—H J=4, 9 Hz)

3-(S,1-diacetylsemicarbazonomethyl)-2-cephem-4-carboxylic acid methylester.

IR $\nu_{max}^{KBr}$ cm$^{-1}$: 1780($\beta$-lactam), 1742(ester).
UV $\lambda_{max}^{EtOH}$ nm ($\epsilon$): 258(17,200).
NMR(DMSO-d$_6$, ppm): 2.06(3H,s,SCOCH$_3$), 2.14(3H,s,NCOCH$_3$), 3.63(2H,s,C$_6$H$_5$CH$_2$—), 3.72(3H,s,COOCH$_3$), 5.12(1H,d,C$_6$—H J=4 Hz),

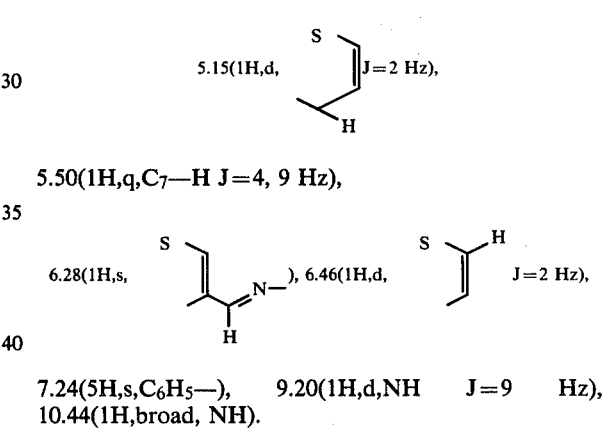

5.50(1H,q,C$_7$—H J=4, 9 Hz), 7.24(5H,s,C$_6$H$_5$—), 9.20(1H,d,NH J=9 Hz), 10.44(1H,broad, NH).

EXAMPLE 14

(1) A solution of 0.1 g of the triacetyl derivative obtained in Example 13 and 70 mg of DDQ is 5 ml of anhydrous dioxane is stirred at 100° C. for 5 hours. The solvent is distilled off under reduced pressure and the residue is chromatographed on a column of silica gel and developed with benzene-ethyl acetate(1:3). The fractions containing the desired product are combined, and the solvent is distilled off to give 0.075 g (87%) of 3-(5-acetylamino-1,3,4-thiadiazol-2-yl)-7-phenylacetamido-2-cephem-4-carboxylic acid methyl ester, colourless needles, melting point: 226°-230° C.(decomp.).

(2) A solution of 0.2 g of diacetyl derivative and 0.16 g of DDQ in 10 ml of anhydrous dioxane is stirred at 40° C. for 18 hours. The solvent is distilled off under reduced pressure, and the residue is chromatographed on a column of silica gel [developing with ethyl acetate-benzene (1:1)]. The procedure gives 0.162 g (89%) of the corresponding 3-thiadiazole derivative described in (1).

Melting point: 225°-229° C. (decomp.).

IR $\nu_{max}^{KBr}$ cm$^{-1}$; 1782($\beta$-lactam), 1740(ester), 1696, 1665 (CONH).

UV $\lambda_{max}^{EtOH}$ nm(ε): 250(5,100), 313(17,700).

NMR(DMSO-d$_6$,ppm): 2.22(3H,s,NHCOCH$_3$), 3.60(2H,s,C$_6$H$_5$—CH$_2$—), 3.68(3H,s,COOCH$_3$) 5.23(1H,d,C$_6$—H J=4 Hz), 5.50 (1H,q,C$_7$—H J=4, 9 Hz),

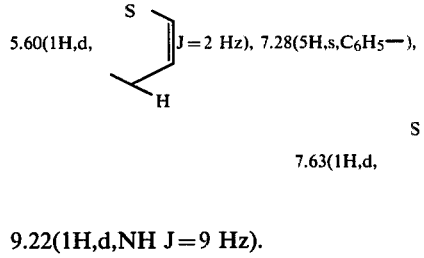

5.60(1H,d, J=2 Hz), 7.28(5H,s,C$_6$H$_5$—), 7.63(1H,d, J=2 Hz), 9.22(1H,d,NH J=9 Hz).

EXAMPLE 15

To a solution of 60 mg of 3-formyl-7-thienylacetamido-2-cephem-4-carboxylic acid in 0.5 ml of anhydrous tetrahydrofuran is added diphenyl diazomethane.

The mixture is stirred at room temperature for 30 minutes and the solvent is evaporated under reduced pressure. The residue is triturated with petroleum ether and ethyl acetate to give 81 mg of 3-formyl-7-thienylacetamido-2-cephem-4-carboxylic acid benzhydryl ester as colourless needles. Melting point: 144°–145° C. (decomp.)

EXAMPLE 16

To a solution of 1.5 g of 3-formyl-2-cephem-4-carboxylic acid benzhydryl ester (obtained in Example 15) in 6 ml of anhydrous dimethyl sulfoxide is added 0.33 g of thiosemicarbazide, and the mixture is stirred at 45° C. for 5 hours. The reaction mixture is poured into cold water and the aqueous solution is extracted with ethyl acetate. The organic layer is washed with a saturated aqueous solution of sodium chloride and dried on anhydrous sodium sulfate, and the solvent is thereafter removed to give 1.82 g of 3-thiosemicarbazone.

IR $\nu_{max}^{KBr}$ cm$^{-1}$: 1775(β-lactam), 1740, 1265, 700(COOCH—(C$_6$H$_5$)$_2$) 1670(CONH).

UV $\lambda_{max}^{EtOH}$ nm (ε): 323(39,700).

NMR(DMSO-d$_6$, ppm):

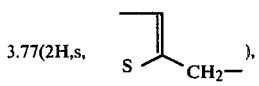

3.77(2H,s, S-CH$_2$—), 5.10(1H,d,J=4 Hz, C$_6$—H), 5.42(1H,q,J=9, 4 Hz, C$_7$—H), 6.11(1H,s,C$_4$—H), 6.75(1H,s,COOCH—), 7.09(1H,s,C$_3$-vinyl H), 6.9–7.4 (3H,m,thienyl), 7.2–7.4(10H,m,COOCH (C$_6$H$_5$)$_2$), 7.71(1H,s,C$_2$—H), 7.85, 8.11(each br.s,NH$_2$), 9.20(1H,d, J=9 Hz,CONH), 11.33(br.s.NH).

EXAMPLE 17

A mixture of 1 g of 3-thiosemicarbazone-2-cephem-4-carboxylic acid benzhydryl ester (obtained in Example 16), 10 ml of acetic anhydride and 3 ml of acetic acid is stirred at 50° C. overnight. The solvent is evaporated under reduced pressure and the residue is chromatographed on a column of silica gel [developed with benzene-ethyl acetate (1:1)] to give 1.1 g. of the diacetate.

IR $\lambda_{max}^{KBr}$ cm$^{-1}$: 1783(β-lactam), 1740, 1240, 700(COOCH (C$_6$H$_5$)$_2$), 1660, 1610(acetyl), 1660(CONH).

UV $\lambda_{max}^{EtOH}$ nm(ε): 240(20,900).

NMR(DMSO-d$_6$, ppm): 2.01(6H,s,acetyl),

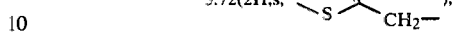

3.72(2H,s, S-CH$_2$—), 4.94(1H,d,J=4 Hz, C$_6$—H), 5.32(1H,d,J=2 Hz,C$_4$—H), 5.43 (1H,q,J=9,4 Hz,C$_7$—H), 6.33(1Hs,C$_3$-vinyl H), 6.71 (1H,d,J=2 Hz,C$_2$—H), 6.73(1H,s,COOCH—), 7.2–7.5(10H,m,COOCH(C$_6$H$_5$)$_2$), 6.9–7.4(3H,m,-thienyl),9.25(1H,d,J=9 Hz,CONH)

EXAMPLE 18

To a solution of 1 g of 3-diacetylthiosemicarbazone-4-benzhydryl ester (obtained in Ex. 17) in 30 ml of anhydrous dioxane are added 1.1 g of DDQ and the solution is stirred at 45°–48° C. After 10 hours, the separated crystals are filtered off, and the filtrate is concentrated under reduced pressure. The residue is chromatographed on a column of silica gel [developed with benzene-ethyl acetate (1:1)] to give 0.7 g of 3-(5-acetylamino-1,3,4-thiadiazol-2-yl)-7-thienylacetamido-2-cephem-4-carboxylic acid benzhydryl ester.

IR $\nu_{max}^{KBr}$ cm$^{-1}$: 1780(β-lactam), 1740, 1700[CO$_2$CH (C$_6$H$_5$)$_2$], 1690(—NHCOCH$_3$), 1670(—CONH).

UV $\lambda_{max}^{EtOH}$ nm (ε): 315(17,100).

NMR(DMSO-d$_6$, ppm): 2.19(3H,s,NHCOCH$_3$),

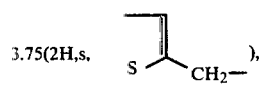

3.75(2H,s, S-CH$_2$—), 5.10(1H,d,J=4 Hz, C$_6$—H), 5.48(1H,q,J=8 Hz,4 Hz,C$_7$—H), 5.78(1H,J=2 Hz,C$_4$—H), 6.74(1H,s,CO$_2$-CH—), 7.1–7.4 (10H,m,CO$_2$CH(C$_6$H$_5$)$_2$), 6.8–7.4(3H,m,thienyl-H), 7.60 (1H,d,J=2 Hz,C$_2$—H), 9.23(1H,d,J=8 Hz,—CONH).

EXAMPLE 19

A mixture of 0.12 g of the 3-acetylaminothiadiazol-4-benzhydryl ester (obtained in Ex.18), 0.5 ml of anisole and 2 ml of trifluoroacetic acid is stirred for 20 minutes at room temperature. After removal of the solvent under reduced pressure, the residue is triturated with the addition of ethyl acetate. The precipitates are collected by filtration, and washed with ethyl acetate to yield 0.08 g of 3-(5-acetylamino-1,3,4-thiadiazol-2-yl)-7-thienylacetamido-2-cephem-4-carboxylic acid as colourless crystals.

IR $\nu_{max}^{KBr}$ cm$^{-1}$: 2200–3000(CO$_2$H), 1770(β-lactam), 1682 (NHCOCH$_3$), 1645(CONH).

NMR(DMSO-d$_6$, ppm): 2.18(3H,s,NHCOCH$_2$),

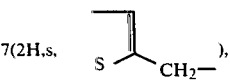

3.77(2H,s, S-CH$_2$—), 5.23(1H,d,J=4 Hz, C$_6$—H), 5.51(1H,d,J=2 Hz,C$_4$—H), 5.50(1H,q,J=8 Hz,4 Hz,C$_7$—H), 6.9–7.3(3H,m,thienyl H), 7.50(1H,d,J=2 Hz,C$_2$—H), 9.21(1H,d,J=8 Hz,CONH), 12.5(1H,broad s,NHCOCH$_3$).

Physical constants of Na salt.

IR $\nu_{max}^{KBr}$ cm$^{-1}$: 3400, 1610(—COO$^-$), 1760($\beta$-lactam), 1680 (NHCOCH$_3$), 1660(CONH).

UV $\lambda_{max}^{H2O}$ nm ($\epsilon$): 235(11,500), 315(16,700).

EXAMPLE 20

To a solution of 63.2 mg of $\Delta^2$-3-N-acetylthiadiazolyl-4-benzhydryl ester (obtained in Ex. 18) in 3 ml of dichloromethane is added 21 mg of m-chloroperhenzoic acid with stirring at room temperature. After 2 hours, the starting material has completely disappeared upon thin layer chromatography. Rf values of starting material and product are assigned to 0.84 and 0.23, respectively [developed with ethyl acetate-methylene chloride (5:1) on a silica gel plate.]

The resulting mixture is concentrated under reduced pressure. The residue is first treated with zinc chloride and acetyl chloride, and is then worked up by the method described in Ex. 19, to give 33 mg of 3-(5-acetylamino-1,3,4-thiadiazol-2-yl)-7-thienylacetamido-3-cephem-4-carboxylic acid. This product is completely identical with an authentic sample obtained in Ex. 10.

EXAMPLE 21

To a solution of 5 g of 3-formyl-7-thienylacetamido-3-cephem-4-carboxylic acid benzhydryl ester in 10 ml of dimethylsulfoxide is added 1.5 g of 4,4-dimethylthiosemicarbazide. The mixture is stirred for 30 minutes at room temperature, poured into cold water and shaken with ethyl acetate. The organic layer is washed with a saturated aqueous solution of sodium chloride, dried over sodium sulfate, and the solvent is evaporated. The residue is chromatographed on a column of silica gel [eluting with benzene—ethyl acetate (2:1)] to give 4.15 g of the corresponding 4,4-dimethylthiosemicarbazone as pale yellow needles. Melting point: 175°-176° C.

IR $\nu_{max}^{KBr}$ cm$^{-1}$: 1782($\beta$-lactam), 1720(ester), 1672(amide).

UV $\lambda_{max}^{EtOH}$ nm($\epsilon$): 343 (23,700).

NMR(DMSO-d$_6$, ppm); 3.21(6H,s), 3.65, 4.17(2H,dd,J=18 Hz), 3.76(2H,s), 5.23(1H,d,J=5 Hz), 5.70(1H,q,J=5,9 Hz), 6.8-6.9(3H,m), 7.2-7.6(11H,m), 8.40(1H,s), 9.17 (1H,d,J=9 Hz), 11.22(1H,br.s).

EXAMPLE 22

A solution of 0.9 g of 3-(4,4-dimethylthiosemicarbazonomethyl)-7-thienylacetamido-3-cephem-4-carboxylic acid benzhydryl ester obtained in Example 21 in 10 ml of acetic anhydride and 3 ml of acetic acid is stirred at 50° C. for 10 minutes. Excess acetic anhydride and acetic acid are distilled off under reduced pressure, and the residue is extracted with ethyl acetate. The organic layer is washed with a saturated aqueous solution of sodium chloride, dried over sodium sulfate, and the solvent is evaporated to give 0.95 g of the monoacetyl thiosemicarbazone.

IR $\nu_{max}^{KBr}$ cm$^{-1}$: 1782($\beta$-lactam), 1715(ester), 1690(acetyl), 1650(amide).

UV $\lambda_{max}^{EtOH}$ nm ($\epsilon$): 265(17,400).

NMR(DMSO-d$_6$, ppm); 2.06(3H,s), 2.85(6H,s), 3.44(2H,br.s), 3.73(2H,s), 5.12(1H,d,J=5 Hz), 5.80(1H,q,J=5, 9 Hz), 6.81(1H,s), 6.85-6.90(3H,m), 7.2-7.5(11H,m), 9.12 (1H,d,J=9 Hz).

EXAMPLE 23

Four grams of the monoacetyl thiosemicarbazone obtained in Example 22 is dissolved in 30 ml of anhydrous dioxane and to the solution is added 1.56 g of 2,3-dichloro-5,6-dicyanobenzoquinone (DDQ), followed by stirring at 50° C. for 3 hours. After cooling, the reaction mixture is filtered and the filter cake is washed with a small amount of dioxane. The combined filtrate is evaporated to dryness under reduced pressure and the residue is chromatographed on a column of silica gel [eluting with ethyl acetate-n-hexane (5:1)] to give 2.8 g of 3-(5-dimethylamino-1,3,4-thiadiazol-2-yl)-7-thienylacetamido-3-cephem-4-carboxylic acid benzhydryl ester as pale yellow plates.

Melting point: 190°-191° C.

IR $\nu_{max}^{KBr}$ cm$^{-1}$: 1785($\beta$-lactam), 1727(ester), 1663(amide).

UV $\lambda_{max}^{EtOH}$ nm ($\epsilon$): 343(13,100).

NMR(DMSO-d$_6$, ppm); 2.89(6H,s), 3.78, 4.05(2H,dd,J=18 Hz), 3.75(2H,s), 5.23(1H,d,J=5 Hz), 5.81(1H,q,J=9, 5 Hz), 6.92(1H,s), 6.8-6.9(2H,m), 7.0-7.5(11H,m), 9.21(1H, d,J=9 Hz).

EXAMPLE 24

(1) A solution of 6.8 g of the 4,4-dimethyl thiosemicarbazone obtained in Example 21 in 30 ml of anhydrous dioxane is added 2.75 g of DDQ, followed by stirring at room temperature for 10 minutes. After cooling, the reaction mixture is filtered and the filter cake is washed with a small amount of dioxane. The combined filtrate is evaporated to dryness under reduced pressure and the residue is chromatographed on a column of silica gel [eluting with benzene-ethyl acetate (3:1)] to give 3.5 g. of 3-(5-dimethylamino-1,3,4-thiadiazol-2-yl)-7-thienylacetamido-3-cephem-4-carboxylic acid benzhydryl ester.

(2) To a solution of 1 g of 4,4-dimethylthiosemicarbazone obtained in Example 21 in 5 ml of anhydrous dioxane is added 1 g of chloranil and the mixture is allowed to stand overnight. After working up in the manner described for (1), the crystals of 3-(5-dimethylamino-1,3,4-thiadiazol-2-yl)-7-thienylacetoamido-3-cephem-4-carboxylic acid benzhydryl ester weighed 0.73 g.

EXAMPLE 25

To a suspension of 150 mg of 3-thiadiazole-4-carboxylic acid benzhydryl ester obtained in Example 23 or 24 in 2 ml of anisole is added 2 ml of trifluoroacetic acid under stirring and ice-cooling. After 20 min., the solvent is distilled off under reduced pressure and the residue is dissolved in a saturated aqueous solution of sodium bicarbonate. The aqueous solution is charged on a column of Amberlite XAD-II and developed with water and then 10% ethyl alcohol. The fractions containing the desired product are combined and lyophilized to give 107 mg of sodium 3-(5-dimethylamino-1,3,4-thiadiazol-2-yl)-7-thienylacetamido-3-cephem-4-carboxylate.

IR $\nu_{max}^{KBr}$ cm$^{-1}$: 1770($\beta$-lactam), 1660(amide), 1603(carboxylate).

UV $\lambda_{max}^{H2O}$ nm($\epsilon$): 335(15,300).

NMR(DMSO-d$_6$, ppm): 3.17(6H,s), 3.75, 4.05(2H,dd,J=18 Hz), 3.95(2H,s), 5.24(1H,d,J=5 Hz), 5.76(1H,d,J=5 Hz), 7.05-7.10(2H,m), 7.45(1H,m).

EXAMPLE 26

To a suspension of 4.16 g of phosphorus pentachloride in 20 ml of dichloromethane is added 3.16 g of pyridine with stirring at −15° C. To the resulting mixture is added a solution of 3.04 g of 3-(5-dimethylamino-1,3,4-thiadiazol-2-yl)-7-thienylacetamido-3-cephem-4-carboxylic acid benzhydryl ester in 50 ml of dichloromethane with stirring at 0°–5° C. and stirring is continued at 10° C. for an additional hour. To the mixture is added 7.5 ml of methyl alcohol at −20° C. and the mixture is stirred for 2 hours. The reaction mixture is poured into cold water. After neutralization with sodium bicarbonate, the mixture is extracted with ethyl acetate. The organic layer is washed with a saturated aqueous solution of sodium chloride, dried over sodium sulfate, and the solvent is evaporated under reduced pressure. The residue is chromatographed on a column of silica gel [eluting with ethyl acetate-n-hexane (5:1)] to give 2.162 g. (91%) of 3-(5-dimethylamino-1,3,4-thiadiazol-2-yl)-7-amino-3-cephem-4-carboxylic acid benzhydryl ester.

IR $\nu_{max}^{KBr}$ cm$^{-1}$: 3400(amino), 1770($\beta$-lactam), 1720(ester), 1608(double bond).

UV $\lambda_{max}^{EtOH}$ nm($\epsilon$): 340(9900).

NMR(CDCl$_3$, ppm): 2.23(2H,br.s), 2.90(6H,s), 3.67, 4.15 (2H,dd,J=18 Hz), 4.77(1H,d,J=5 Hz), 4.97(1H,d,J=5 Hz), 6.95(1H,s), 7.1–7.4(10H,m).

EXAMPLE 27

To a solution of 1.04 g of 3-formyl-7-thienylacetamido-3-cephem-4-carboxylic acid benzhydryl ester in 4 ml of dimethylsulfoxide is added 0.354 g of morpholinothiocarbonylhydrazide. The mixture is stirred for 2 hours at room temperature, poured into cold water and shaken with 700 ml of ethyl acetate. The organic layer is washed with a saturated aqueous solution of sodium chloride, dried over sodium sulfate, and the solvent is evaporated. The residue is chromatographed on a column of silica gel [eluting with ethyl acetate - n-hexane (5:3)] to give 0.75 g of 3-morpholinothiocarbonylhydrazonomethyl-7-thienylacetamido-3-cephem-4-carboxylic acid benzhydryl ester.

IR $\nu_{max}^{KBr}$ cm$^{-1}$: 1783($\beta$-lactam), 1720(ester), 1680(amide).

UV $\lambda_{max}^{EtOH}$ nm($\epsilon$): 347(25,200).

NMR(DMSO-d$_6$, ppm): 3.4–4.0(10H,m), 3.80(2H,s), 5.20(1H, d,J=5 Hz), 5.78(1H,q,J=5, 8 Hz), 6.92(1H,s), 6.85(2H, m), 7.2–7.6(11H,m), 8.33(1H,s), 9.19(1H,d,J=8 Hz), 11.40(1H,s).

EXAMPLE 28

To a solution of 430 mg of the hydrazone obtained in Example 27 in 5 ml of anhydrous dioxane is added 162 mg. of DDQ and the mixture is stirred at room temperature for 10 minutes. After cooling, the reaction mixture is filtered and the filter cake is washed with a small amount of dioxane. The combined filtrate is evaporated to dryness under reduced pressure and the residue is chromatographed on a column of silica gel [eluting with ethyl acetate—n-hexane (5:3)] to give 340 mg of 3-(5-morpholino-1,3,4-thiadiazol-2-yl)-7-thienylacetamido-3-cephem-4-carboxylic acid benzhydryl ester as colourless needles.

Melting point: 209°–211° C.

IR $\nu_{max}^{KBr}$ cm$^{-1}$: 1778($\beta$-lactam), 1720(ester), 1641(amide).

UV $\lambda_{max}^{EtOH}$ nm($\epsilon$): 338(13,700).

NMR(DMSO-d$_6$, ppm): 3.2–3.9(8H,m), 3.75(2H,s), 3.79, 4.03 (2H,dd,J=18 Hz), 5.23(1H,d,J=5 Hz), 5.83(1H,q,J=5, 9 Hz), 6.92(1H,s), 7.1–7.6(11H,m), 6.8–6.9(2H,m), 9.23 (1H,d,J=9 Hz).

Elemental analysis: Calcd. for C$_{32}$H$_{29}$N$_5$O$_5$S$_3$; C, 58.25; H, 4.43; N, 10.61; S, 14.58. Found: C, 58.05; H, 4.23; N, 10.39; S, 14.56.

EXAMPLE 29

To a solution of 11 g of 3-formyl-7-thienylacetamido-3-cephem-4-carboxylic acid benzhydryl ester in 30 ml of dimethylsulfoxide is added 2.1 g of thioacetohydrazide. The mixture is stirred for 3 hours, poured into cold water and shaken with ethyl acetate. The organic layer is washed with a saturated aqueous solution of sodium chloride, dried over sodium sulfate, and the solvent is removed in vacuo to give 7.7 g of the corresponding thioacetohydrazone as pale yellow needles.

Melting point: 199°–201° C.(decomp.).

IR $\nu_{max}^{KBr}$ cm$^{-1}$: 1780($\beta$-lactam), 1718(ester), 1755(amide), 1600(double bond).

UV $\lambda_{max}^{EtOH}$ nm($\epsilon$): 363 (32,800).

NMR(DMSO-d$_6$, ppm): 2.54(3H,s), 3.75(2H,s), 3.60, 4.15 (2H,dd,J=18 Hz), 5.22(1H,d,J=5 Hz), 5.82(1H,q,J=5, 9Hz), 6.92(1H,s), 6.9(2H,m), 7.0–7.6(11H,m), 8.40(1H,s), 9.2(1H,d,J=9 Hz).

The preparation of thioacetohydrazide is as follows. To a solution of 2.5 g of 100% hydrazine hydrate, 45 ml of 99% ethanol is added 5.3 g of methyl dithioacetate [prepared by the method of R. Mayer, S. Scheithauer; Ber., 99, 1393(1966)] under stirring for 45 min. at −70° C. The mixture is stirred for 30 min., poured into 200 ml of anhydrous ether, cooled at −70° C. The formed crystals are filtered and washed with a small amount of anhydrous ether, dried to give 2.1 g of thioacetohydrazide as colourless needles. Melting point: 73°–75° C. (decomp.)

IR $\nu_{max}^{KBr}$ cm$^{-1}$: 1640, 1538, 1418, 1180, 1130, 1000, 800.

EXAMPLE 30

To a solution of 7.89 g of the thioacetohydrazone obtained in Example 29 in 70 ml of anhydrous dioxane is added 3.2 g of DDQ, followed by stirring at 45° C. for 5 hours. After cooling, the reaction mixture is filtered and the filter cake is washed with a small amount of dioxane. The combined filtrate is evaporated to dryness under reduced pressure and the residue is chromatographed on a column of silica gel and developed with ethyl acetatebenzene (1:1) to give 6.4 g of 3-(5-methyl-1,3,4-thiadiazol-2-yl)-7-thienylacetamido-3-cephem-4-carboxylic acid benzhydryl ester as colourless needles.

Melting point: 192°–194° C. (decomp.).

IR $\nu_{max}^{KBr}$ cm$^{-1}$: 1785($\beta$-lactam), 1730(ester).

UV $\lambda_{max}^{EtOH}$ nm($\epsilon$): 307(11,900).

NMR(DMSO-d$_6$, ppm): 2.5(3H,s), 3.76(2H,s), 3.8, 4.04(2H, dd,J=18 Hz), 5.26(1H,d,J=5 Hz), 5.84(1H,q,J=5, 9 Hz), 6.85(2H,m), 6.91(1H,s), 7.0–7.4(11H,m), 9.22(1H,d, J=9 Hz).

Elemental analysis: Calcd. for C$_{29}$H$_{24}$N$_4$S$_3$; C, 59.16; H, 4.11; N, 9.52; S, 16.34. Found: C, 58.94; H, 3.94; N, 9.64; S, 16.34

EXAMPLE 31

A mixture of 0.2 g of the 3-thiadiazole-4-carboxylic acid benzhydryl ester, 3 ml of anisole and 2 ml of trifluoroacetic acid is stirred for 20 min. under ice-cooling. After removal of solvent under reduced pressure, the residue is triturated with the addition of petroleum ether. The formed crystals are collected by filtration, washed with ether to yield 0.14 g of 3-(5-methyl-1,3,4-thiadiazol-2-yl)-7-thienylacetamido-3-cephem-4-carboxylic acid as pale yellow needles, melting point: 194°-196° C. (decomp.). The crystals are dissolved in a saturated aqueous solution of sodium bicarbonate and the solution is charged on a column of Amberlite XAD-II. After the elution with water and then 10% ethyl alcohol, the fractions containing the desired product are combined and lyophilized to give sodium 3-(5-methyl-1,3,4-thiadiazol-2-yl)-7-thienylacetamido-3-cephem-4-carboxylate.

IR $\nu_{max}^{KBr}$ cm$^{-1}$: 1770($\beta$-lactam), 1660(amide), 1610(carboxylate).

UV $\lambda_{max}^{H2O}$ nm($\epsilon$): 305(12,800).

NMR (D$_2$O, ppm): 2.75(3H,s), 3.78, 4.02(2H,dd,J=18 Hz), 3.91(2H,s), 5.24(1H,d,J=5 Hz), 5.73(1H,d,J=5 Hz), 7.0–7.1(2H,m), 7.3–7.4(1H,m).

EXAMPLE 32

To a suspension of 3.75 g of phosphorus pentachloride in 60 ml of dichloromethane is added 2.844 g of pyridine under stirring at −15° C. To the resulting mixture is added a solution of 3.528 g of the 3-thiadiazole-4-carboxylic acid benzhydryl ester obtained in Example 30 in 60 ml of dichloromethane at −5° C. After stirring for 1 hour at 0° C., to the reaction mixture is added 6.6 g of methanol under stirring at −30° C., and the mixture is poured into cold water, neutralized with sodium bicarbonate. The organic layer is washed with a saturated aqueous solution of sodium chloride, dried over sodium sulfate and the solvent is evaporated. The residue is chromatographed on a column of silica gel [eluting with ethyl acetate—benzene (1:1)] to give 2.3 g of 3-(5-methyl-1,3,4-thiadiazol-2-yl)-7-amino-3-cephem-4-carboxylic acid benzhydryl ester as pale yellow needles.

Melting point: 162-164° C.(decomp.).

IR $\nu_{max}^{KBr}$ cm$^{-1}$: 1790($\beta$-lactam), 1735(ester), 1620(double bond).

UV $\lambda_{max}^{EtOH}$ nm($\epsilon$): 307(10,500).

NMR(CDCl$_3$, ppm): 2.1–2.4(2H,br), 2.46(3H,s), 3.68, 4.06 (2H,dd), 4.80(1H,d,J=5 Hz), 4.97(1H,d,J=5 Hz), 6.92 (1H,s), 7.0–7.5(10H,m).

EXAMPLE 33

To a solution of diketene (0.103 g 13 m mol) dissolved in 2 ml of dry dichloromethane, bromine (0.224 g 14 m mol) in 7.25 ml of dry dichloromethane is added dropwise with stirring at −40° C.

Stirring and cooling are maintained for 15 min. The reaction mixture is added dropwise to a solution of 0.439 g (1 m mol) of 7-amino-3-(5dimethylamino-1,3,4-thiadiazol-2-yl)-3-cephem-4-carboxylic acid benzhydryl ester and 0.101 g (1 m mol) of triethylamine in 7 ml of dry dichloromethane with stirring at −30° C.

The solution is evaporated under reduced pressure to give 0.540 g of yellowish powder. This powder is dissolved in 20 ml of acetone, and to the solution are added 83.6 mg of thiourea and 92.4 mg of sodium bicarbonate with stirring. After 15 min., 5 ml of water is added to this reaction mixture and the solution is stored at room temperature overnight.

The acetone is removed in vacuo and replaced by 50 ml of ethyl acetate.

The solution is washed with a saturated aqueous solution of sodium chloride, dried over anhydrous sodium sulfate and evaporated to dryness.

The residue is chromatographed on a column of silica gel [eluting with ethyl acetate-acetone (3:1)] to give 262 mg. of colourless fine needles.

Melting point: 197°-198° C.

IR $\nu_{max}^{KBr}$ cm$^{-1}$: 1779($\beta$-lactam), 1721(ester), 1660(amide).

NMR(CDCl$_3$, ppm):

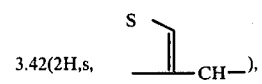

3.92(6H,s,N(CH$_3$)$_2$), 3.69 and

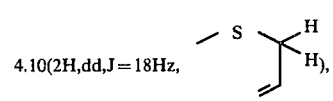

5.10(1H,d, J=5 Hz,C$_6$—H), 5.87(1H,q,J=9, 5 Hz,C$_7$—H), 6.18(1H,s,CO$_2$CH—), 7.1–7.4(10H,m,(C$_6$H$_5$)$_2$—), 8.81(1H,d,J=9 Hz, CONH).

EXAMPLE 34

A mixture of 0.2 g of the 7-aminothiazolacetamido-3-dimethylthiazol-4-carboxylic acid benzhydryl ester (obtained in Example 33), 3 ml of anisole and 2 ml of trifluoroacetic acid is stirred for 20 min. at room temperature. After removal of the solvent under reduced pressure, the residue suspended in 50 ml of water is treated with Amberlite IR-45(bufferized at pH 4). The aqueous solution is filtered and the filtrate is lyophilized to give 0.04 g of 3-(5-dimethylamino-1,3,4-thiadiazol-2-yl)-[2-(2-aminothiazol-4-yl)acetamido]-3-cephem-4-carboxylic acid as yellowish powder.

IR $\nu_{max}^{KBr}$ cm$^{-1}$: 1765($\beta$-lactam), 1655(amide), 1605(carboxylate).

NMR(DMSO-d$_6$, ppm):

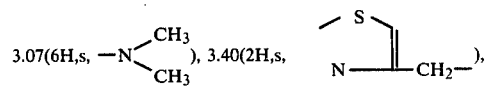

3.77 and

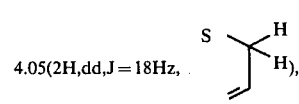

5.18(1H,d, J=5 Hz, C$_6$—H), 5.74(1H,q,J=9, 5 Hz,C$_7$—H),

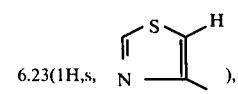

6.92(2H,br.s.NH$_2$), 8.93(1H,d,J=9 Hz, CONH).

| Antibacterial spectra (mcg/ml, agar dilution method) | | | |
|---|---|---|---|
| Strain of microorganism | Product of this example | Cephaloridine | Cefazolin |
| S. aureus 209P | 0.39 | ≦0.2 | ≦0.2 |
| S. aureus 1840 | 1.56 | 0.39 | 0.78 |
| E. coli NIHJ JC-2 | 1.56 | 3.13 | 1.56 |
| E. coli 0-111 | ≦0.2 | 1.56 | 0.78 |
| E. coli T-7 | 3.13 | >100 | 50 |
| K. pneumoniae DT | 0.39 | 1.56 | 1.56 |
| P. vulgaris Eb53 | ≦0.2 | >100 | 100 |

EXAMPLE 35

A mixture of 439 mg (1 m mol) of 7-amino-3-(5-dimethylamino-1,3,4-thiadiazol-2-yl)-3-cephem-4-carboxylic acid benzhydryl ester and 200 mg (1.12 m mol) of 2,4-dioxo-5-phenyl-1,3-dioxolane in 5 ml of dry dichloromethane is stirred at room temperature for 15 hours.

After removal of the solvent under reduced pressure, the residue is chromatographed on a column of silica gel [eluting with ethyl acetate-benzene (1:1)] to give 400 mg of 7-D-(−)-α-hydroxyphenylacetamido-3-(5-dimethylamino-1,3,4-thiadiazol-2-yl)-3-cephem-4-carboxylic acid benzhydryl ester as colourless cubics.

Melting point: 189°–190° C.

IR $\nu_{max}^{KBr}$ cm$^{-1}$: 3300(OH), 1799(β-lactam), 1721(ester), 1679(amide).

NMR(DMSO-d$_6$, ppm):

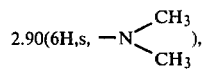

3.30(1H,br.s,—OH), 3.75 and

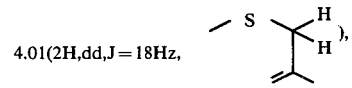

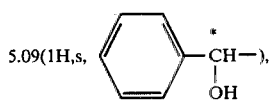

5.20(1H,d,J=5 Hz,C$_6$—H), 5.82(1H,q,J=9, 5 Hz, C$_7$—H), 6.84(1H,s,CO$_2$CH—), 7–7.5(15H,m,phenyl), 8.87(1H,d, J=9 Hz, CONH).

EXAMPLE 36

A mixture of 0.1 g of the benzhydryl ester (obtained in Example 35), 2 ml of anisole and 1 ml of trifluoroacetic acid is stirred at 0° C. for 10 min. and then at room temperature for 20 min.

After removal of the solvent under reduced pressure, the residue is triturated with the addition of absolute ether to give 0.065 g of the trifluoroacetic acid salt of 7-D(−)-α-hydroxyphenylacetamido-3-(5-dimethylamino-1,3,4-thiadiazol-2-yl)-3-cephem-4-carboxylic acid as pale yellow crystals.

Melting point: 152°–162° C. (decomp.).

IR $\nu_{max}^{KBr}$ cm$^{-1}$: 1773(β-lactam), 1660(amide), 1620(carboxylate).

NMR(DMSO-d$_6$, ppm):

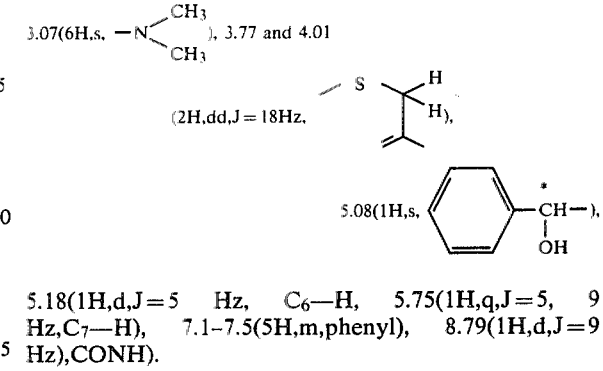

5.18(1H,d,J=5 Hz, C$_6$—H), 5.75(1H,q,J=5, 9 Hz,C$_7$—H), 7.1–7.5(5H,m,phenyl), 8.79(1H,d,J=9 Hz),CONH).

EXAMPLE 37

A solution of 0.15 g of the salt (obtained in Example 36) in 3 ml of water is charged on a column of Amberlite XAD-II, and developed with water and then 10% EtOH. The fractions containing the desired product are combined and lyophilized to give 0.12 g of 7-D(−)-α-hydroxyphenylacetamido-3-(5-dimethylamino-1,3,4-thiadiazol-2-yl)-3-cephem-4-carboxylic acid.

IR $\nu_{max}^{KBr}$ cm$^{-1}$: 1775(β-lactam), 1670(amide), 1620(carboxylate).

NMR(DMSO-d$_6$, ppm): 3.07(6H,s,CH$_3$—), 3.77, 4.01(2H,ABq,C$_2$—H J=18 Hz),

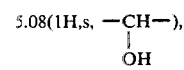

5.18(1H,d,C$_6$—H J=5 Hz), 5.75(1H,q,C$_7$—H, J=5, 9 Hz), 6.3(1H,br.s.,—OH), 7.1–7.5(5H,m,phenyl), 8.79(1H,d,—NH J=9 Hz).

EXAMPLE 38

A mixture of 0.2 g of benzhydryl 3-(5-methyl-1,3,4-thiadiazol-2-yl)-7-amino-3-cephem-4-carboxylate (obtained in Example 31) and 0.1 g of 2,4-dioxo-5-phenyl-1,3-dioxolane in 10 ml of anhydrous dichlromethane is stirred overnight at room temperature. The reaction mixture is concentrated in vacuo, and the residue is chromatographed on a column of silica gel [developed with benzene-ethyl acetate (1:1)] to give 0.2 g of benzhydryl 7-D(−)-α-hydroxyphenylacetamido-3-(5-methyl-1,3,4-thiadiazol-2-yl)-3-cephem-4-carboxylate as colourless needles.

Melting point; 188°–190° C.(decomp.).

IR $\nu_{max}^{KBr}$ cm$^{-1}$: 1770(β-lactam), 1718(ester), 1670(amide).

NMR(CDCl$_3$, ppm); 2.48(3H,s,CH$_3$), 3.88(2H,dd,C$_2$—H J=19 Hz), 5.05(1H,d,C$_6$—H J=5 Hz),

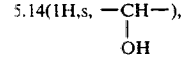

5.85(1H, q, C$_7$—H J=5, 9 Hz), 6.92(1H,s,COOCH<), 7.0–7.6 (15H,m,phenyl), 8.06(1H,d,NH J=9 Hz).

EXAMPLE 39

A mixture of 0.10 g of benzhydryl 7-D(−)-α-hydroxyphenylacetamido-3-(5-methyl-1,3,4-thiadiazol-2-yl)-3-cephem-4-carboxylate (obtained in Example 38), 1 ml of anisole and 3 ml of trifluoroacetic acid is stirred for 20 minutes at room temperature. After removal of the solvent under reduced pressure, the residue is triturated with the addition of absolute ether. The precipitates are collected by filtration, and washed with ether to give 60 mg 7-D(−)-α-hydroxyphenylacetamido-3-(5-methyl-1,3,4-thiadiazol-2-yl)-3-cephem-4-carboxylic acid as colourless crystals.

Melting point: 146°–152° C. (decomp.)
IR $v_{max}^{KBr}$ cm$^{-1}$: 1780(β-lactam).
NMR(DMSO-d$_6$, ppm): 2.70(3H,s,CH$_3$), 3.92(2H,dd,C$_2$—H J=19 Hz),

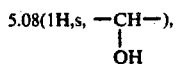
5.08(1H,s, —CH—),
         |
         OH 5.20(1H,d,C$_6$—H J=5 Hz), 5.78(1H, q,C$_7$—H J=5, 9Hz), 7.1–7.5(5H,m,phenyl), 8.85(1H,d, NH J=9 Hz).

EXAMPLE 40

A mixture of 0.13 g of 3-morpholinothiadiazol-4-carboxylic acid benzhydryl ester (obtained in Example 28), 3 ml of anisole and 2 ml of trifluoroacetic acid is stirred for 20 min. at room temperature.

After removal of the solvent under reduced pressure, the residue is triturated with the addition of anhydrous ether. The precipitates are collected by filtration, and dissolved in a saturated aqueous solution of sodium bicarbonate.

The solution is charged on a column of Amberlite XAD-II and developed with water and then 10% EtOH. The fractions containing the desired product are combined and lyophilized to give 66 mg of sodium 3-(5-morpholino-1,3,4-thiadiazol-2-yl)-7-thienylacetamido-3-cephem-4-carboxylate.

IR $v_{max}^{KBr}$ cm$^{-1}$: 1770(β-lactam), 1663(amide), 1600(carboxylate).
NMR(D$_2$O, ppm): 3.5–3.9(8H,m,morpholino protons),

3.93(2H,s,            ) 3.83,

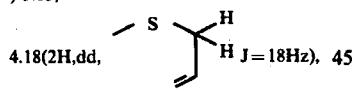
4.18(2H,dd,                    J=18Hz), 5.27(1H,d,C$_6$—H J=5 Hz), 5.74(1H,d,C$_7$—H J=5=5 Hz),

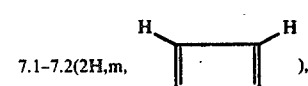
7.1–7.2(2H,m,       ),

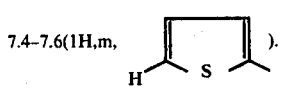
7.4–7.6(1H,m,       ).

EXAMPLE 41

A solution of 0.70 g of 3-formyl-7-thienylacetamido-3-cephem-4-carboxylic acid and 0.24 g of 4,4-dimethyl-thiosemicarbazide in 4 ml of dimethylsulfoxide is stirred for 3 hours at room temperature, diluted with ice-water, and shaken with ethyl acetate. The ethyl acetate layer is washed with a sodium chloride solution, dried over anhydrous sodium sulfate and concentrated under reduced pressure. The residual crystals are filtered and washed with ether to give 0.8 g of the corresponding thiosemicarbazone. Melting point: 165°–168° C.(decomp.)

IR $v_{max}^{Nujol}$ cm$^{-1}$: 1765(β-lactam), 1650(amide).
NMR(DMSO-d$_6$, ppm): 3.22(6H,s,CH$_3$),

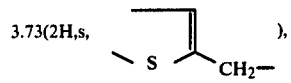
3.73(2H,s,       ), 3.80(2H,ABq,C$_2$—H J=18 Hz), 5.14(1H,d,C$_6$—H J=5 Hz), 5.70(1H,q,C$_7$—H J=4, 9Hz),

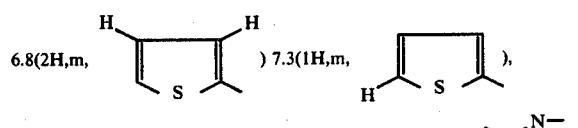
6.8(2H,m,        ) 7.3(1H,m,        ), 8.35(1H,s,     ), 9.14(1H,br.d,NH J=9 Hz).

EXAMPLE 42

0.11 g of the thiosemicarbazone obtained in Example 41 is dissolved in 6 ml of anhydrous dioxane and to the solution is added 50 mg of DDQ, followed by stirring at room temperature for 1 hour. The reaction mixture is filtered and the filter cake is washed with a small amount of dioxane. The combined filtrate is evaporated to dryness under reduced pressure and the residue is filtered, washed with ether. The product is dissolved in tetrahydrofuran and the solution is treated with active carbon. After removal of the active carbon by filtration, the solvent is removed. The residual crystals are filtered and washed with ether to give 80 mg of 3-(5-dimethylamino-1,3,4-thiadiazol-2-yl)-7-thienylacetamido-3-cephem-4-carboxylic acid as pale yellow needles.

Melting point: 172°–174° C.(decomp.).
IR $v_{max}^{Nujol}$ cm$^{-1}$: 1775(β-lactam), 1650(amide).
NMR(DMSO-d$_6$, ppm): 3.08(6H,s,CH$_3$),

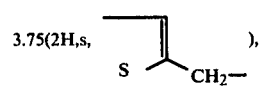
3.75(2H,s,        ), 3.91(2H,ABq,C$_2$—H J=18 Hz), 5.19(1H,d,C$_6$—H J=5 Hz), 5.74(1H,q,C$_7$—H J=5, 9 Hz),

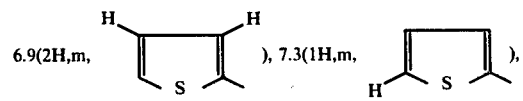
6.9(2H,m,        ), 7.3(1H,m,        ), 9.17(1H,br.d, NH J=9 Hz).

EXAMPLE 43

A mixture of 0.464 g. of benzhydryl 7-amino-3-(5-methyl-1,3,4-thiadiazol-2-yl)-3-cephem-4-carboxylate (obtained in Example 32), 0.378 g of N-t-butoxycarbonyl-D(−)-phenylglycine and 0.634 g of N-cyclohexyl-N'-[2-(4-morpholinyl)-ethyl]-carbodiimide meso-P-toluenesulfonate in 10 ml of absolute tetrahydrofuran is stirred for two houres at room temperature. After removal of the solvent under reduced pressure, the residue is dissolved in ethyl acetate and the solution is washed with water. The ethyl acetate layer is dried over anhydrous sodium sulfate and the solvent is removed in vacuo. The residue is chromatographed on a column of silica gel [developed with benzene-ethyl acetate (1:1)] to give 0.564 g of benzhydryl 7-N-t-butoxycarbonyl-D(−)-phenylglycinamido-3-(5-methyl-1,3,4-thiadiazol-2-yl)-3-cephem-4-carboxylate as colourless needles.

Melting point: 207°–210° C.(decomp.).

IR $\nu_{max}^{KBr}$ cm$^{-1}$: 1790(β-lactam), 1730(ester), 1665(amide).

NMR(CDCl$_3$, ppm):

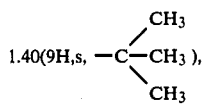

1.40(9H,s, —C(CH$_3$)$_3$), 2.48(3H,s,CH$_3$—), 3.79(2H,dd,C$_2$—H J=19 Hz), 4.98(1H,d,C$_6$—H J=5 Hz),

5.25(1H,d, —CHCO J=7Hz), 5.65(1H,d, —CHCO—J=7Hz),
           |                                  |
           NH                                 NH 5.88(1H,q,C$_7$—H J=5, 9 Hz), 6.92(1H,s,COOCH<), 7.0–7.5(15H,m,phenyl).

EXAMPLE 44

A mixture of 0.30 g of benzhydryl 7-N-t-butoxycarbonyl-D(−)-phenylglycinamido-3-(5-methyl-1,3,4-thiadiazol-2-yl)-3-cephem-4-carboxylate (obtained in Example 43), 3 ml of anisole and 9 ml of trifluoroacetic acid is stirred for 20 minutes at room temperature. After removal of the solvent under reduced pressure, the residue is triturated with the addition of absolute ether. The precipitates are filtered, and washed with ether to give the trifluoroacetic acid salt of the corresponding carboxylic acid. The salt is chromatographed on a column of Amberlite XAD-II [developed with 10% EtOH] to give 0.117 g of 7-D(−)-phenylglycinamido-3-(5-methyl-1,3,4-thiadiazol-2-yl)-3-cephem-4-carboxylic acid.

IR $\nu_{max}^{KBr}$ cm$^{-1}$: 1770(β-lactam), 1690(amide), 1600(carboxylate).

NMR (D$_2$O, ppm): 2.72(3H,s,CH$_3$), 3.80(2H,dd,C$_2$—H J=19 Hz), 5.20(1H,d,C$_6$—H J=5 Hz),

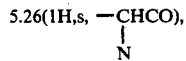

5.26(1H,s, —CHCO),
         |
         N 5.80(1H, d,C$_7$—H J=5 Hz), 7.54(5H,s,phenyl).

EXAMPLE 45

To a suspension of 0.625 g of powdered phosphorous pentachloride in 20 ml of dichloromethane is added 0.474 g of pyridine under stirring at −40° C. To the resulting mixture is added dropwise a solution of 0.422 g of 7-thienylacetamido-3-(5-dimethylamino-1,3,4-thiadiazol-2-yl)-3-cephem-4-carboxylic acid (obtained in Example 42) in 10 ml of dichloromethane, 0.242 g of dimethylaniline and then 0.3 ml of dimethyldichlorosilane under stirring at −40° C. After stirring for 30 minutes at 0° C., to the reaction mixture is added 5 ml of methanol under stirring at −40° C., and the mixture is poured into cold water. The aqueous layer is neutralized to pH 5.5 with an aqueous solution of sodium bicarbonate and washed three times with dichloromethane. The solution is charged on a column of Amberlite XAD-II and eluted with water. The fractions containing the desired product are collected and lyophilized to give 0.140 g of 7-amino-3-(5-dimethylamino-1,3,4-thiadiazol-2-yl)-3-cephem-4-carboxylic acid.

IR $\nu_{max}^{KBr}$ cm$^{-1}$: 1740(β-lactam), 1630(carboxylate).

NMR(DMSO-d$_6$, ppm): 3.00(6H,s,NMe$_2$), 3.60, 4.02(2H,ABq, C$_2$—H J=18 Hz), 4.58(1H,d,C$_6$—H J=5 Hz), 4.95(1H,d, C$_7$—H J=5 Hz).

EXAMPLE 46

To a solution of 0.491 g of benzhydryl 7-amino-3-(5-dimethylamino-1,3,4-thiadiazol-2-yl)-3-cephem-4-carboxylate (obtained in Example 26) in 16 ml of dichloromethane is dropwise added 0.160 g of phenylacetylchloride and 0.10 g of triethylamine with stirring under ice-cooling, and stirring and cooling are maintained for 30 minutes. The reaction mixture is washed with water, dried over anhydrous sodium sulfate and the solvent is removed in vacuo. The residue is chromatographed on a column of silica gel [eluted with benzene-ethyl acetate(1:3)] to give 0.51 g of benzhydryl 7-phenylacetamido-3-(5-dimethylamino-1,3,4-thiadiazol-2-yl)-3-cephem-4-carboxylate.

IR $\nu_{max}^{KBr}$ cm$^{-1}$: 1790 (β-lactam), 1730(ester), 1665(amide).

NMR(DMSO-d$_6$, ppm); 288(6H,s,NMe$_2$), 3.50(2H,s,φCH$_2$—), 3.76, 4.02(2H,ABq,C$_2$—H J=18 Hz), 5.20(1H,d,C$_6$—H J=5 Hz), 5.78(1H,q,C$_7$—H J=8, 5 Hz), 6.84(1H,s,—CHφ$_2$), 7.0–7.4(15H, m,phenyl), 9.18(1H,d,NH J=18 Hz).

EXAMPLE 47

A mixture of 0.3 g of benzhydryl 7-phenylacetamido-3-(5-dimethylamino-1,3,4-thiadiazol-2-yl)-3-cephem-4-carboxylate (obtained in Example 46), 2 ml of anisole and 3 ml of trifluoroacetic acid is stirred for 20 minutes at room temperature. After removal of the solvent under reduced pressure, the residue is triturated with the addition of absolute ether. The precipitates are filtered, washed with ether and dissolved in an aqueous solution of sodium bicarbonate. The solution is charged on a column of Amberlite XAD-II, and eluted with water and then 10% ethanol. The fractions containing the desired product are collected and lyophilized to give 0.2 g of sodium 7-phenylacetamido-3-(5-dimethylamino-1,3,4-thiadiazol-2-yl)-3-cephem-4-carboxylate.

IR $\nu_{max}^{KBr}$ cm$^{-1}$: 1768(β-lactam), 1660(amide), 1610(carboxylate).

NMR(D$_2$O, ppm): 3.12(6H,s,NMe$_2$), 3.70(2H,s,—CH$_2$φ), 3.71, 4.02(2H,dd,C$_2$—H J=18 Hz), 5.19(1H,d,C$_6$—H J=5 Hz), 5.70(1H,d,C$_7$—H J=5 Hz), 7.38(5H,s,phenyl).

EXAMPLE 48

A mixture of 0.25 g of benzhydryl 7-amino-3-(5-dimethylamino-1,3,4-thiadiazol-2-yl)-3-cephem-4-carboxylate, 0.1 g of syn 2-methoxyiminophenylacetic acid and 0.24 g of N-cyclohexyl-N'-[2-(4-morpholinyl)-ethyl]-carbodiimide-meso-p-toluenesulfonate in 15 ml of absolute tetrahydrofuran is stirred for 3 hours at room temperature. After removal of the solvent under reduced pressure, the residue is dissolved in ethyl acetate and the solution is washed with water. The organic layer is dried over anhydrous sodium sulfate and the solvent is removed in vacuo. The residue is chromatographed on a column of silica gel [eluted with dichloromethane-ethyl acetate (2:1)] to give 0.14 g of benzhydryl 7-(2-methoxyimino-2-phenylacetamido)-3-(5-dimethylamino-1,3,4-thiadiazol-2-yl)-3-cephem-4-carboxylate.

IR $\nu_{max}^{KBr}$ cm$^{-1}$: 1790($\beta$-lactam), 1725(ester), 1663(amide).

NMR(CDCl$_3$, ppm): 2.96(6H,s,N(CH$_3$)$_2$), 3.74, 4.26(2H,dd, C$_2$H J=18 Hz), 5.17(1H,d,C$_6$—H J=5 Hz), 6.04(1H,q,C$_7$—H J=4, 8 Hz), 7.00(1H,d,NH J=8 Hz), 7.02(1H,s,—C$\underline{H}\phi_2$), 7.2–7.7(15H,m,phenyl).

EXAMPLE 49

A mixture of 0.11 g of benzhydryl 7-(2-methoxyimino-2-phenylacetamido)-3-(5-dimethylamino-1,3,4-thiadiazol-2-yl)-3-cephem-4-carboxylate (obtained in Example 48), 2 ml of anisole and 4 ml of trifluoroacetic acid is stirred for 30 minutes at room temperature. After removal of the solvent under reduced pressure, the residue is triturated with the addition of absolute ether. The precipitates are filtered, and washed with ether to give 0.058 g of 7-(2-methoxyimino-2-phenylacetamido)-3-(5-dimethylamino-1,3,4-thiadiazol-2-yl)-3-cephem-4-carboxylic acid.

IR $\nu_{max}^{Nujol}$ cm$^{-1}$: 1800($\beta$-lactam).

NMR(DMSO-d$_6$, ppm): 3.11(6H,s,N(CH$_3$)$_2$), 3.84,4.08(2H,dd, C$_2$—H J=18 Hz), 3.95(3H,s,OCH$_3$), 5.32(1H,d,C$_6$—H J=5 Hz), 5.94(1H,q,C$_7$—H J=5, 9 Hz), 7.3–7.7(5H,m,phenyl), 9.79(1H,d,NH J=9 Hz).

EXAMPLE 50

To a solution of 0.46 g of benzhydryl 7-amino-3-(5-dimethylamino-1,3,4-thiadiazol-2-yl)-3-cephem-4-carboxylate (obtained in Example 26) in 40 ml of dichloromethane is added 0.197 g of $\alpha$-sulfophenylacetyl chloride and 0.102 g of N,N-dimethylaniline with stirring at 5° C. After 30 minutes, the reaction mixture is washed with 10% hydrochloric acid and then a saturated aqueous solution of sodium chloride. The organic layer is dried over anhydrous sodium sulfate and the solvent is removed under reduced pressure.

The residue is dissolved in 3 ml of anisole and 4 ml of trifluoroacetic acid with stirring at room temperature, and stirring is maintained for 20 minutes. After removal of the solvent in vacuo, the residue is triturated with the addition of absolute ether. The precipitates are filtered, and dissolved in an aqueous solution of sodium bicarbonate. The solution is charged on a column of Amberlite XAD-II and eluted with water. The fractions containing the desired product are combined and lyophilized to give 0.133 g of 7-D(−)-$\alpha$-sulfophenylacetamido-3-(5-dimethylamino-1,3,4-thiadiazol-2-yl)-3-cephem-4-carboxylic acid sodium salt.

IR $\nu_{max}^{KBr}$ cm$^{-1}$: 1762($\beta$-lactam), 1672(amide), 1608(carboxylate).

NMR (D$_2$O, ppm): 3.10(6H,s,NMe$_2$), 3.63,3.88(2H,dd,C$_2$—H J=18 Hz),

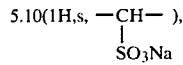

5.10(1H,s, —CH— ),
              |
              SO$_3$Na 5.17(1H,d,C$_6$—H J=5 Hz), 5.76(1H, d,C$_7$—H J=5 Hz), 7.3–7.8(5H,m,phenyl).

EXAMPLE 51

To a solution of 0.493 g of benzhydryl 7-amino-3-(5-dimethylamino-1,3,4-thiadiazol-2-yl)-3-cephem-4-carboxylate (obtained in Example 26) in 22 ml of dichloromethane are added 0.5 g of t-butylphenylmalonyl chloride and 0.121 g of N,N-dimethylaniline with stirring under ice-cooling. After 30 minutes, the reaction mixture is washed with an aqueous solution of sodium bicarbonate and then water, and the solvent is removed under reduced pressure. The residue is chromatographed on a column of silica gel [eluted with n-hexane-ethyl acetate(1:3)] to give 0.5 g of benzhydryl 7-(2-t-butoxycarbonylphenylacetamido)-3-(5-dimethylamino-1,3,4-thiadiazol-2-yl)-3-cephem-4-carboxylate (1:1 mixture of diastereoisomer).

IR $\nu_{max}^{KBr}$ cm$^{-1}$: 1790($\beta$-lactam), 1730(ester), 1690(amide).

D-(−): NMR(DMSO-d$_6$, ppm); 1.38(s,t-Bu), 2.88(s,NMe$_2$), 3.80, 4.05(ABq, C$_2$—H J=18 Hz), 4.71(s,—C$\underline{H}\phi$), 5.27(d,C$_6$—H J=5 Hz), 5.80(q,C$_7$—H J=5,8 Hz), 6.83(s,—C$\underline{H}\phi_2$), 7.0–7.4(m,phenyl), 9.37(d,NH J=8 Hz).

L-(+): NMR(DMSO-d$_6$, ppm): 1.41(s,t-Bu), 2.90(s,NMe$_2$), 3.67, 3.91(ABq,C$_2$—H J=18 Hz), 4.69(s,—C$\underline{H}\phi$), 5.14(d, C$_6$—H J=5 Hz), 5.72(q,C$_7$—H J=5,8 Hz), 6.83(s,C$\underline{H}\phi_2$), 9.26 (d,NH J=8 Hz).

EXAMPLE 52

To a suspension of 0.4 g of the 3-thiadiazole benzhydryl ester (obtained in Example 51) in 2 ml of anisole is added 3 ml of trifluoroacetic acid with stirring under ice-cooling. The mixture is allowed to react at room temperature for one hour, and the solvent is removed under reduced pressure. The residue is triturated with the addition of absolute ether. The precipitates are filtered, and dissolved in an aqueous solution of sodium bicarbonate. The solution is charged on a column of Amberlite XAD-II and eluted with water to give 7-($\alpha$-carboxyphenylacetamido)-3-(5-dimethylamino-1,3,4-thiadiazol-2-yl)-3-cephem-4-carboxylic acid sodium salt (1:1 mixture of diastereoisomer).

IR $\nu_{max}^{KBr}$ cm$^{-1}$: 1764($\beta$-lactam), 1660(amide), 1603(carboxylate).

D-(−): NMR(D$_2$O, ppm): 3.11(s,NMe$_2$), 3.71, 4.03(ABq,C$_2$—H J=18 Hz), 5.00(s,—CH$\phi$), 5.22(d,C$_6$—H J=4 Hz), 5.78(d, C$_7$—H J=4 Hz), 7.42(s,phenyl).

l-(+): NMR(D$_2$O, ppm): 3.11(s,NMe$_2$), 3.66, 3.95(ABq,C$_2$—H J=18 Hz), 5.00(s,—CH$\phi$), 5.18(d,C$_6$—H J=4 Hz), 5.78(d, C$_7$—H J=4 Hz), 7.42(s,phenyl).

EXAMPLE 53

A mixture of 1.1 g of benzhydryl 7-amino-3-(5-dimethylamino-1,3,4-thiadiazol-2-yl)-3-cephem-4-carboxylate (obtained in Example 26), 0.68 g of N-t-butoxycarbonyl-D(−)-p-hydroxyphenylglycine and 1.12 L g of N-cyclohexyl-N'-[2-(4-morpholinyl)ethyl]-carbodiimide meso-p-toluenesulfonate in 16 ml of absolute tetrahydrofuran is stirred for 3 hours at room temperature. After removal of the solvent under reduced pressure, the residue is dissolved in ethyl acetate and the solution is washed with water. The organic layer is dried over anhydrous sodium sulfate and the solvent is removed in vacuo. The residue is chromatographed on a column of silica gel [eluted with dichloromethane-ethyl acetate(2:1)] to give 0.705 g of benzhydryl 7-N-t-butoxycarbonyl-D(−)-p-hydroxyphenylglycinamido-3-(5-dimethylamino-1,3,4-thiadiazol-2-yl)-3-cephem-4-carboxylate.

IR $\nu_{max}^{Nujol}$ cm$^{-1}$: 1785($\beta$-lactam), 1720(ester).

NMR(DMSO-d$_6$,ppm): 1.40(9H,s,—C(CH$_3$)$_3$), 2.90(6H,s,NMe$_2$), 3.83(2H,ABq,C$_2$—H J=18 Hz), 5.16(1H,d,C$_6$—H J=4 Hz), 5.20(1H,d,—CHCO J=7 Hz), 5.84(1H,q,C$_7$—H J=4, 9 Hz), 6.85(1H,s,—CH$\phi_2$), 7.1–7.4(15H,m,NH and phenyl), 9.14(1H,d,NH J=9 Hz).

EXAMPLE 54

A mixture of 0.44 g of the 3-thiadiazole benzhydryl ester (obtained in Example 53), 3.0 ml of anisole and 5 ml of trifluoroacetic acid is stirred for 45 minutes at room temperature. After removal of the solvent under reduced pressure, the residue is triturated with the addition of absolute ether. The precipitates are filtered, and washed with ether to give the trifluoroacetic acid salt of the corresponding carboxylic acid. The salt is chromatographed on a column of Amberlite XAD-II [eluted with H$_2$O and then 13% ethanol] to give 0.18 g of 7-D(—)-p-hydroxyphenylglycineamido-3-(5-dimethylamino-1,3,4-thiadiazol-2-yl)-3-cephem-4-carboxylic acid.

IR $\nu_{max}^{Nujol}$ cm$^{-1}$; 1770($\beta$-lactam), 1685(amide), 1610(carboxylate).

NMR(DMSO-d$_6$, ppm); 3.02(6H,s,NMe$_2$), 3.60, 3.96(2H,dd,C$_2$—H J=18 Hz), 4.90(1H,d,C$_6$—H J=5 Hz), 5.02(1H,d, —CHCO J=7Hz), 5.62(1H,q,C$_7$—J=5, 8 Hz).

EXAMPLE 55

A mixture of 0.540 g of benzhydryl 7-amino-3-(5-dimethylamino-1,3,4-thiadiazol-2-yl)-3-cephem-4-carboxylate (obtained in Example 26), 0.450 g of N-t-butoxycarbonyl-D(—)-phenylglycine and 0.556 g of N-cyclohexyl-N'-[2-(4-morpholinyl)ethyl]-carbodiimide meso-p-toluenesulfonate in 10 ml of absolute tetrahydrofuran is stirred for 40 minutes at room temperature. After working up as described in Example 43, 0.495 g of benzhydryl 7-N-t-butoxycarbonyl-D(—)-phenylglycineamido-3-(5-dimethylamino-1,3,4-thiadiazol-2-yl)-3-cephem-4-carboxylate is obtained.

Melting point: 175°–8° C.(decomp.).

IR $\nu_{max}$ cm$^{-1}$: 1790($\beta$-lactam), 1725(ester), 1695, 1665 (amide).

NMR(CDCl$_3$, ppm): 1.40(s,—C(CH$_3$)$_3$), 2.90(s,NMe$_2$), 3.57, 4.06(ABq,C$_2$—H J=18 Hz), 4.94 (d,C$_6$—H J=5 Hz), 5.22 (d, —CH—J=7Hz),
        |
        N 5.68(d,NHCOO—J=7 Hz), 5.82(q,C$_7$—H J=5, 9 Hz), 6.75(d,CONH J=9 Hz), 6.95(s,—CH$\phi_2$), 7.0–7.5(-m,aromatic H).

EXAMPLE 56

A mixture of 0.495 g of the 3-thiadiazole benzhydryl ester (obtained in Example 55), 5 ml of anisole and 15 ml of trifluoroacetic acid is stirred for 30 minutes at room temperature. After removal of the solvent under reduced pressure, the residue is triturated with the addition of absolute ether. The precipitates are filtered, and washed with ether. The precipitates are dissolved in water, and the solution is neutralized with sodium bicarbonate. The separated crystals are filtered, and washed with water, ethanol and then ether to give 0.15 g of 7-D(—)-phenylglycineamido-3-(5-dimethylamino-1,3,4-thiadiazol-2-yl)-3-cephem-4-carboxylic acid.

IR $\nu_{max}^{KBr}$ cm$^{-1}$: 1760($\beta$-lactam), 1610(carboxylate).

NMR (D$_2$O, ppm): 3.30(s,NMe$_2$), 3.70(broad s,C$_2$—H), 5.16(d, C$_6$—H J=5 Hz),

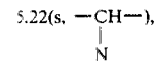
5.22(s, —CH—),
        |
        N 5.80(d,C$_7$—H J=5 Hz), 7.5(s,aromatic H).

EXAMPLE 57

A mixture of 0.202 g of benzhydryl 7-amino-3-(5-methyl-1,3,4-thiadiazol-2-yl)-3-cephem-4-carboxylate (obtained in Example 32), 0.08 g of syn 2-methoxyiminophenylacetic acid and 0.190 g of N-cyclohexyl-N'-[2-(4-morpholinyl)-ethyl]-carbodiimide-meso-p-toluenesulfonate in 5 ml of absolute tetrahydrofuran is stirred for 3.5 hours at room temperature. After removal of the solvent under reduced pressure, the residue is dissolved in ethyl acetate and the solution is washed with water. The ethyl acetate layer is dried over anhydrous sodium sulfate and the solvent is removed in vacuo. The residue is chromatographed on a column of silica gel [eluted with dichloromethane-ethyl acetate(3:1)] to give 0.09 g of benzhydryl 7-(2-methoxyimino-2-phenylacetamido)-3-(5-methyl-1,3,4-thiadiazol-2-yl)-3-cephem-4-carboxylate.

IR $\nu_{max}^{KBr}$ cm$^{-1}$: 1795($\beta$-lactam), 1730(ester), 1667(amide).

NMR(CDCl$_3$, ppm): 2.52(3H,s,CH$_3$), 3.73, 4.17(2H,dd,C$_2$—H, J=19 Hz), 4.06(3H,s,—OCH$_3$), 5.18(1H,d,C$_6$—H J=5 Hz), 6.08(1H,q,C$_7$—H J=5, 9 Hz), 6.98(1H,s,—CH$\phi_2$), 7.2–7.7 (15H,m,phenyl).

EXAMPLE 58

A mixture of 0.07 g of benzhydryl 7-(2-methoxyimino-2-phenylacetamido)-3-(5-methyl-1,3,4-thiadiazol-2-yl)-3-cephem-4-carboxylate (obtained in Example 59), 2 ml of anisole and 4 ml of trifluoroacetic acid is stirred for 30 minutes at room temperature. After removal of the solvent under reduced pressure, the residue is triturated with the addition of absolute ether. The precipitates are filtered, and washed with ether to give 0.046 g of 7-(2-methoxyimino-2-phenylacetamido)-3-(5-methyl-1,3,4-thiadiazol-2-yl)-3-cephem-4-carboxylic acid.

IR $\nu_{max}^{Nujol}$ cm$^{-1}$; 1780($\beta$-lactam).

NMR(DMSO-d$_6$, ppm); 2.73(3H,s,CH$_3$), 3.96(3H,s,OCH$_3$), 3.98 (2H,br.s,C$_2$—H), 5.36(1H,d,C$_6$—H J=5 Hz), 5.98(1H, q, C$_7$—H J=5, 8 Hz), 7.3–7.7(5H,m,phenyl H), 9.82(1H, d,NH J=8 Hz).

EXAMPLE 59

To a suspension of 1.5 g of phosphorous pentachloride in 13 ml of dichloromethane is added 1.2 g of pyridine in 13 ml of dichloromethane under stirring at −40° C. To the resulting mixture is added 1.6 g of benzhydryl 7-thienylacetamido-3-(5-acetylamino-1,3,4-thiadiazol-2-yl)-3-cephem-4-carboxylate in 32 ml of dichloromethane at −40° C. After stirring for one hour at 0° C., to the reaction mixture is added 6 g of n-butanol under stirring at −40° C. After working up as described in Example 26, the obtained residue is chromatographed on a column of silica gel [eluting with ethyl acetate-dichloromethane (1:1)] to give 0.522 g of benzhydryl 7-amino-3-(5-acetylamino-1,3,4-thiadiazol-2-yl)-3-cephem-4-carboxylate as pale yellow needles.

Melting point: 165°–170° C.(decomp.).

IR $\nu_{max}^{KBr}$ cm$^{-1}$: 1780 ($\beta$-lactam), 1725(ester), 1695(amide).

NMR(CDCl$_3$, ppm): 1.80(broad, NH$_2$), 2.30(s,COCH$_3$), 3.72, 3.98(ABq,C$_2$—H J=18 Hz), 4.86(d,C$_6$—H J=5 Hz), 5.04(d, C$_7$—H J=5 Hz), 6.94(s,—CH$\phi_2$), 7.0–7.4(m,aromatic H).

EXAMPLE 60

A mixture of 0.169 g of the 7-aminobenzhydryl ester obtained in Example 59, 0.125 g of N-tert-butyloxycarbonyl-D-(−)-phenylglycine and 0.125 g of N-cyclohexyl-N'-[2-(4-morpholinyl)-ethyl]-carbodiimide metho-p-toluene sulfonate in 5 ml of absolute tetrahydrofuran is stirred for 12 hours at room temperature. After working up as described in Example 43. The obtained residue is chromatographed on a column of silica gel [eluted with ethyl acetate-benzene (1:1)] to give 0.2 g of benzhydryl 7-[D-(−)-α-(tert-butyloxycarbonylamino)-phenylacetamido]-3-(5-acetylamino-1,3,4-thiadiazol-2-yl)-3-cephem-4-carboxylate as colorless needles.

Melting point: 213°–215° C.

IR $\nu_{max}^{KBr}$ cm$^{-1}$: 1790($\beta$-lactam), 1720(ester), 1700(amide).

NMR[CDCl$_3$-DMSO-d$_6$(trace), ppm]: 1.45[s,—C(CH$_3$)$_3$], 2.23 (s,—COCH$_3$), 3.63, 3.95(ABq, C$_2$—H, J=18 Hz), 5.05(d, C$_6$—H, J=5 Hz),

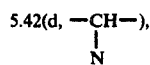
5.42(d, —CH—),
       |
       N 5.86(q,C$_7$—H, J=5 Hz, 9 Hz),

6.10(d,
—C—),
 |
 NH 6.91(s,—CH$\phi_2$), 7–7.6(m,arom), 9.0(d,—CONH,9 Hz), 12.2(broad s,NHAC).

EXAMPLE 61

To a suspension of 0.20 g of the 3-thiadiazole benzhydryl ester obtained in Example 60 in 3 ml of anisole is added 5 ml of trifluoroacetic acid under stirring at 0° C. After stirring for 30 minutes at room temperature, the mixture is concentrated in vacuo. The residue is triturated with the addition of petroleum ether. The formed precipitates are collected by filtration, washed with petroleum ether to yield 0.10 g of the corresponding trifluoroacetic acid salt. The salt is chromatographed on a column of Amberlite XAD-II [eluted with 10% ethanol] to give 0.07 g of 7-D-(−)-α-aminophenylacetamido-3-(5-acetylamino-1,3,4-thiadiazol-2-yl)-3-cephem-4-carboxylic acid.

IR $\nu_{max}^{KBr}$ cm$^{-1}$: 1770($\beta$-lactam), 1680(amide), 1600(carboxylate).

NMR(D$_2$O, ppm): 2.38(s,COCH$_3$), 3.82, 4.02(ABq,-C$_2$—H J=18 Hz), 5.32(d,C$_6$—H J=5 Hz), 5.35(s, —CH—),
      |
      N 5.90(d,C$_7$—H J=5 Hz), 7.60(s,aromatic H).

EXAMPLE 62

To a solution of 0.163 g of benzhydryl 7-amino-3-(5-acetylamino-1,3,4-thiadiazol-2-yl)-3-cephem-4-carboxylate (obtained in Example 59) in 5 ml of dichloromethane is dropwise added 0.109 g of ω-bromoacetoacetyl bromide and then 0.025 g of pyridine under stirring for 30 minutes at −40° C. The reaction mixture is washed with water, dried over anhydrous sodium sulfate and the solvent is evaporated under reduced pressure. The residue is dissolved in 2 ml of DMA, and to the solution is added 0.025 g of thiourea, followed by stirring for 40 minutes at room temperature. The reaction mixture is poured into water, shaken with ethyl acetate and the organic layer is washed with water, dried over anhydrous sodium sulfate. After removal of the solvent under reduced pressure, the residue is chromatographed on a column of silica gel [eluting with ethyl acetate-tetrahydrofuran (2:1)] to give 0.10 g of benzhydryl 7-[2-(2-aminothiazol-4-yl)acetamido]-3-(5-acetylamino-1,3,4-thiadiazol-2-yl)-3-cephem-4-carboxylate.

IR $\nu_{max}^{KBr}$ cm$^{-1}$; 1785($\beta$-lactam), 1725(ester, 1680(amide).

NMR(DMSO-d$_6$, ppm); 2.20(s,COCH$_3$), 3.42(s,—CH$_2$—), 3.86, 4.10 (ABq,C$_2$—H J=18 Hz), 5.29(d,C$_6$—H J=5 Hz), 5.87(q,C$_7$—H J=5, 9 Hz),

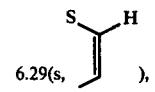
6.29(s,   ), 6.81(s,—CH$\phi_2$), 7.0–7.4(m, aromatic H).

EXAMPLE 63

A mixture of 0.100 g of the 3-thiadiazole benzhydryl ester (obtained in Example 62), 2 ml of anisole and 5 ml of trifluoroacetic acid is stirred for 30 minutes at room temperature. After removal of the solvent under reduced pressure, the residue is triturated with the addition of ether. The precipitates are filtered, washed with ether. 0.080 g of 7-[2-(2-aminothiazol-4-yl)acetamido[-3-(5-acetylamino-1,3,4-thiadiazol-2-yl)-3-cephem-4-carboxylic acid is obtained.

IR $\nu_{max}^{KBr}$ cm$^{-1}$: 1770($\beta$-lactam), 1670(amide), 1620(carboxylate).

NMR(DMSO-d$_6$, ppm): 2.22(s,COCH$_3$), 3.56(s,—CH$_2$—), 3.86, 4.17 (ABq,C$_2$—H J=18 Hz), 5.29(d,C$_6$—H J=5 Hz), 5.84(q,C$_7$—H J=5 Hz, 9 Hz),

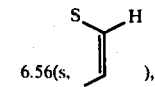
6.56(s,   ), 9.14(d,CONH J=9 Hz).

| Strain of microorganism | Antibacterial spectra (mcg/ml, agar dilution method) | |
|---|---|---|
| | Product of this Example | Cefazolin |
| S. aureus 209P | 0.39 | ≦0.2 |
| E. coli NIHJ | 0.39 | 1.56 |
| E. coli 0-111 | ≦0.2 | 0.78 |
| E. coli T-7 | 12.5 | 25 |
| K. pneumoniae DT | ≦0.2 | 1.56 |
| K. pneumoniae GN3835 | 0.78 | 1.56 |
| P. vulgaris IF03988 | ≦0.2 | 3.13 |
| P. mirabilis GN4359 | ≦0.2 | 3.13 |
| P. morganii IFO 3168 | 3.13 | 25 |
| P. rettgeri 8(TN0336) | ≦0.2 | ≦0.2 |
| P. rettgeri GN4733 | ≦0.2 | 25 |
| Cit. freundii GN99 | 3.13 | 12.5 |
| Cit. freundii GN1706 | 3.13 | >100 |

EXAMPLE 64

A solution of 5.0 g of 7-(5-carbobenzoxyamino-5-carboxyvaleramido)-3-formyl-ceph-3-em-4-carboxylic acid and 1.3 g of 4,4-dimethylthiosemicarbazide in 28 ml of dimethylsulfoxide is stirred for 3 hours at room temperature, diluted with ice-water, and shaken with ethyl acetate. The ethyl acetate layer is washed with a sodium chloride solution, dried over anhydrous sodium sulfate and concentrated under reduced pressure. The residue is triturated with ether until solidified, filtered and washed with ether to give 2.6 g of the corresponding thiosemicarbazone.

IR $\nu_{max}^{KBr}$ cm$^{-1}$: 1780($\beta$-lactam).

NMR(DMSO-d$_6$, ppm): 3.22(s,NMe$_2$), 3.86, 4.06(ABq,C$_2$—H J=18 Hz), 5.14(d,C$_6$—H J=5 Hz), 5.70(q,C$_7$—H J=5, 9 Hz), 5.00(s,—CH$_2\phi$), 7.30(s,aromatic H), 7.48(d,NHCO$_2$ J=9 Hz), 8.36(s, —CH=N—), 8.86(d,NH J=9 Hz).

EXAMPLE 65

2.5 g of the thiosemicarbazone obtained in Example 64 are dissolved in 25 ml of anhydrous dioxane and to the solution is added 1.0 g of DDQ, followed by stirring at room temperature for one hour. The reaction mixture is filtered and the filter cake is washed with a small amount of dioxane. The combined filtrate is evaporated to dryness under reduced pressure and the residue is filtered, washed with ether. The product is dissolved in tetrahydrofuran and the solution is treated with active carbon. After removal of the active carbon by filtration, the solvent is removed. The residual crystals are filtered and washed with ether to give 2.1 g of 7-(5-carbobenzoxyamino-5-carboxyvaleramido)-3-(5-dimethylamino-1,3,4-thiadiazol-2-yl)-ceph-3-em-4-carboxylic acid as pale yellow crystals.

IR $\gamma_{max}^{KBr}$ cm$^{-1}$: 1783($\beta$-lactam).

NMR(DMSO-d$_6$, ppm); 3.06(s,NMe$_2$), 3.80, 4.02(ABq,C$_2$—H J=18 Hz), 5.00(s,—CH$_2\phi$), 5.17(d,C$_6$—H J=5 Hz), 5.71 (q,C$_7$—H J=5, 8 Hz), 7.30(s,aromatic H).

EXAMPLE 66

To a suspension of 2.0 g of the 3-thiadiazole-4-carboxylic acid obtained in Example 65 in 60 ml of dichloromethane is dropwise added 0.7 g of triethylamine, 3.0 g of N,N-dimethylaniline and then 1.12 g of dimethyldichlorosilane under stirring below 20° C., followed by stirring at room temperature for 30 minutes. To the resulting solution is added 1.5 g of well powdered phosphorus pentachloride at −50° C. After stirring for 1.5 hours at −5° C., to the reaction mixture is added 12 ml of methanol under stirring at −40° C., followed by stirring at room temperature for 30 minutes. The mixture is poured into cold water and the aqueous layer is washed with dichloromethane, adjusted to pH 6 with 10% sodium hydroxide solution. The solution is washed with dichloromethane and adjusted to pH 3.0 with 10% phosphoric acid. After concentration to one third of its original volume, the separated crystals are filtered, and washed with water, acetone and then ether to give 0.52 g of 7-amino-3-(5-dimethylamino-1,3,4-thiadiazol-2-yl)-ceph-3-em-4-carboxylic acid as colourless crystals.

EXAMPLE 67

To a solution of 9.5 g of 7-(D-5-tert-butylbenzoylamino-5-carboxyvaleramido)-3-formyl-3-cephem-4-carboxylic acid in 40 ml of dimethylsulfoxide is added 1.9 g of thio acetohydrazide. The mixture is stirred for 1 hour at room temperature, poured into cold water and shaken with ethyl acetate. The ethyl acetate layer is washed with water, dried over anhydrous sodium sulfate, and the solvent is removed in vacuo. The residue is triturated with absolute ether. The precipitates are filtered and washed with ether to give 8.8 g of the corresponding thiosemicarbazone.

IR $\nu_{max}^{KBr}$ cm$^{-1}$: 1780($\beta$-lactam), 1720(-COOH), 1640, 1540 (amide).

NMR(DMSO-d$_6$, ppm); 1.30(s,—C(CH$_3$)$_3$), 2.54(s,—CSCH$_3$), 3.52, 4.04(ABq,C$_2$—H, J=18 Hz), 5.16(d,C$_6$—H, J=5 Hz), 5.75(q,C$_7$—H, J=5 Hz,9 Hz), 7.40

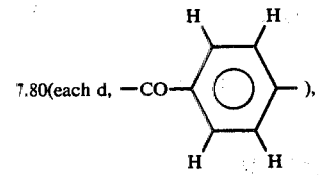

7.80(each d, —CO—⟨ ⟩—), 8.40(d,—NHCO$\phi$, J=9 Hz), 8.42(s,—CH=N—), 8.90(d,CONH, J=9 Hz).

EXAMPLE 68

To a solution of 8 g of the thiosemicarbazone obtained in Example 67 in 50 ml of dioxane is added 3.14 g DDQ under stirring at room temperature. After one hour, the reaction mixture is filtered and the filtrate is concentrated under reduced pressure to give 8 g of 7-(D-5-tert-butylbenzoylamino-5-carboxyvaleramido)-3-(5-methyl-1,3,4-thiadiazol-2-yl)-3-cephem-4-carboxylic acid.

IR $\nu_{max}^{KBr}$ cm$^{-1}$: 1795($\beta$-lactam), 1720(COOH), 1650, 1540(amide).

NMR(DMSO-d$_6$, ppm): 1.30(s,—C(CH$_3$)$_3$), 2.78(s, —CH$_3$), 5.20 (d,C$_6$—H, J=5 Hz), 5.78(q,C$_7$—H, J=5 Hz, 9 Hz),

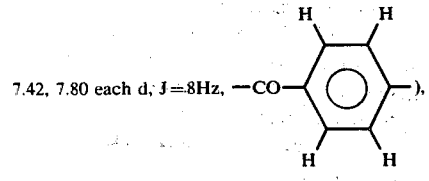

7.42, 7.80 each d, J=8Hz, —CO—⟨ ⟩—), 8.90(d,J=9 Hz,—CONH—).

EXAMPLE 69

To a suspension of 5.75 g of the 3-thiadiazole-4-carboxylic acid obtained in Example 68 in 75 ml of dichloromethane is added 2.5 g of triethylamine. 9 g of N,N-dimethylaniline and then 4.4 g of dimethyldichlorosilane under stirring below 20° C. After stirring for 30 minutes at room temperature, to the reaction mixture is added 4.6 g of powdered phosphorous pentachloride under stirring at −50° C. After stirring for 1.5 hours at −5° C., to the resulting mixture is added 25 ml of methanol at −40° C. The mixture is stirred for 30 minutes at room temperature, poured into cold water and an aqueous layer is neutralized to pH 6 with 10% sodium hydroxide solution. After removal of N,N-dimethylaniline by extraction with dichloromethane, the aqueous layer is adjusted to pH 3 with 10% hydrochloric acid. The resulting mixture is concentrated to give 1 g of 7-amino-3-(5-methyl-1,3,4-thiadiazol-2-yl)-3-cephem-4-carboxylic acid.

IR $\nu_{max}^{KBr}$ cm$^{-1}$: 1805, 1608, 1550.

NMR(CF$_3$COOD, ppm): 3.18(s,CH$_3$), 4.16(s,C$_2$—H), 5.58(s,C$_6$—H and C$_7$—H).

EXAMPLE 70

To a solution of 8 g of the 3-thiadiazole-4-carboxylic acid obtained in Example 68 in 30 ml of tetrahydrofuran is added 3.5 g of diphenyldiazomethane. The mixture is stirred at room temperature for 1 hour and the solvent is evaporated in vacuo. The residue is triturated with hexane-ethylacetate (3:2) to give the corresponding benzhydryl ester. The crude ester is chromatographed on a column of silica gel [developing with ethyl acetate-dichloromethane (1:3)] to give benzhydryl 7-(D-5-tert-butylbenzoylamino-5-benzhydryloxycarbonyl-valeramido)-3-(5-methyl-1,3,4-thiadiazol-2-yl)-3-cephem-4-carboxylate.

IR $\nu_{max}^{KBr}$ cm$^{-1}$: 1790($\beta$-lactam), 1730(ester), 1660, 1650 (amide).

NMR(CDCl$_3$, ppm): 1.28(s,—C(CH$_3$)$_3$), 2.50(s,CH$_3$), 3.56, 3.96 (ABq,C$_2$—H, J=18 Hz),

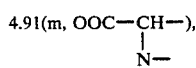

4.91(m, OOC—CH—),
          |
          N—

4.93(d,C$_6$—H J=5 Hz), 5.81(q,C$_7$—H, J=5 Hz, 9 Hz), 6.91, 6.97(each s, —CH$\phi_2$), 7.09(d,J=9 Hz,CONH), 7.1-7.5(m,arom),

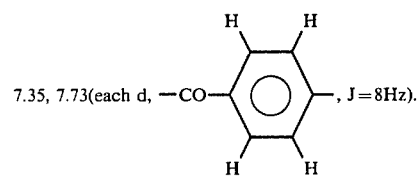

7.35, 7.73(each d, —CO—⟨⟩—, J=8Hz).

EXAMPLE 71

A solution of 5.0 g of 7-(5-phthaloylamino-5-carboxyvaleramido)-3-formyl-ceph-3-em-4-carboxylic acid and 1.3 g of 4,4-dimethylthiosemicarbazide in 30 ml of dimethylsulfoxide is stirred for 3 hours at room temperature, diluted with ice-water, and shaken with ethyl acetate. The organic layer is washed with an aqueous solution of sodium chloride, dried over anhydrous sodium sulfate and concentrated under reduced pressure. The residual crystals are filtered and washed with ether to give 5.1 g of the corresponding thiosemicarbazone.

IR $\nu_{max}^{KBr}$ cm$^{-1}$: 1780($\beta$-lactam).

NMR(DMSO-d$_6$, ppm): 3.23(s,NMe$_2$), 3.84, 4.08(ABq,C$_2$—H J=18 Hz), 5.12(d,C$_6$—H J=5 Hz), 5.73(q,C$_7$—H J=5, 9 Hz), 8.33(s,—CH=N—), 8.87(d,NH J=9 Hz).

EXAMPLE 72

Three grams of the thiosemicarbazone obtained in Example 71 are dissolved in 25 ml of anhydrous dioxane and to the solution is added 1.15 g of DDQ, followed by stirring at room temperature for 1 hour. The reaction mixture is filtered and the filter cake is washed with a small amount of dioxane. The combined filtrate is evaporated to dryness under reduced pressure and the residue is triturated with the addition of absolute ether. The precipitates are filtered, and washed with ether. The product is dissolved in tetrahydrofuran and the solution is treated with active carbon. After removal of the active carbon by filtration, the solvent is removed. The residual crystals are filtered and washed with ether to give 2,1 g of 7-(5-phthaloylamino-5-carboxyvaleramido)-3-(5-dimethylamino-1,3,4-thiadiazol-2-yl)-ceph-3-em-4-carboxylic acid as pale yellow crystals.

IR $\nu_{max}^{KBr}$ cm$^{-1}$: 1782($\beta$-lactam).

NMR(DMSO-d$_6$, ppm): 3.20(s,NMe$_2$), 3.88, 4.05(ABq,C$_2$—H J=18 Hz), 5.12(d,C$_6$—H J=5 Hz), 5.69 (q,C$_7$—H J=5, 9 Hz), 8.87(d,NH J=9 Hz).

EXAMPLE 73

To a suspension of 2.0 g of the 3-thiadiazole-4-carboxylic acid obtained in Example 72 in 50 ml of dichloromethane are dropwise added 0.7 g of triethylamine, 3.0 g of N,N-dimethylaniline and then 1.12 g of dimethyldichlorosilane under stirring below 20° C., followed by stirring at room temperature for 30 minutes. To the resulting solution is added 1.5 g of powdered phosphorus pentachloride at −50° C. After stirring for 1.5 hours at −5° C., to the reaction mixture is added 10 ml of methanol under stirring at −40° C., followed by stirring at room temperature for 30 minutes. The mixture is poured into cold water and the aqueous layer is washed with dichloromethane, adjusted to pH 6 with 10% sodium hydroxide solution. The solution is washed with dichloromethane to remove separated N,N-dimethylaniline and adjusted to pH 3.0. After concentration to one third of its original volume, the separated crystals are filtered, and washed with water, acetone and then ether to give 0.55 g of 7-amino-3-(5-dimethylamino-1,3,4-thiadiazol-2-yl)-ceph-3-em-4-carboxylic acid.

EXAMPLE 74

To a solution of 25 g of 7-(D-5-tert-butylbenzoylamino-5-carboxyvaleramido)-3-formyl-3-cephem-4-carboxylic acid in 50 ml of tetrahydrofuran is added 20 g of diphenyldiazomethane. The mixture is stirred for 1 hour at room temperature and the solvent is evaporated under reduced pressure. The residue is triturated with petroleum ether and the precipitates are chromatographed on a column of silica gel [developing with ethyl acetate-n-hexane (1:1)] to give 40 g of benzhydryl 7-(D-5-tert-butylbenzoylamino-5-benzhydryloxycarbonylvaleramido)-3-formyl-3-cephem-4-carboxylate.

IR $\nu_{max}^{KBr}$ cm$^{-1}$: 1800($\beta$-lactam), 1735(ester), 1650-1670(amide).

EXAMPLE 75

The solution of 17.3 g of the benzhydryl ester obtained in Example 74 and 2 g of thioacetohydrazine in 30 ml of dimethylsulfoxide is stirred for 2 hours at room temperature. The reaction mixture is poured into cold water, and shaken with ethyl acetate. The ethyl acetate layer is washed with water, dried over anhydrous sodium sulfate and concentrated in vacuo to give 19.6 g of the corresponding thiosemicarbazone.

IR $\nu_{max}^{KBr}$ cm$^{-1}$: 1800($\beta$-lactam), 1735(ester), 1670(amide).

EXAMPLE 76

To a solution of 1.5 g of the thiosemicarbazone obtained in Example 7 in 20 ml of tetrahydrofuran is added 0.6 g of diphenyldiazomethane. The mixture is allowed to react at room temperature for 20 minutes and the solvent is evaporated under reduced pressure. The residue is triturated with petroleum ether and the precipitates are chromatographed on a column of silica gel [eluting the ethyl acetate-n-hexane (1:1)] to give 1.2 g of the corresponding thiosemicarbazone benzhydryl ester.

EXAMPLE 77

To a solution of 19.6 g of the thiosemicarbazone obtained in Example 76 in 50 ml of dioxane is added 4 g of DDQ, followed by stirring at room temperature for 30 minutes. The reaction mixture is filtered and the filtrate is evaporated to dryness in vacuo. The residue is chromatographed on a column of silica gel [eluting with ethyl acetate dichloromethane (1:3)] to give 12 g of benzhydryl 7-(D-5-tert-butylbenzoylamino-5-benzhydrolyoxycarbonylvaleramido)-3-(5-methyl-1,3,4-thiadiazol-2-yl)-3-cephem-4-carboxylate.

EXAMPLE 78

To a suspension of 4.3 g of pulverized phosphorus pentachloride in 35 ml of dichloromethane is added a solution of 3.25 g of pyridine in 35 ml of dichloromethane under stirring at $-40°$ C.

To the resulting mixture is added 6.4 g of benzhydryl 7-(D-5-tert-butylbenzoylamino-5-benzhydryloxycarbonylvaleramido)-3-(5-methyl-1,3,4-thiadiazol-2-yl)-3-cephem-4-carboxylate in 70 ml of dichloromethane at $-40°$ C. After stirring for 1.5 hours at 0° C., to the reaction mixture is added 7.5 g of methanol under stirring at $-40°$ C. and then stirred for 30 minutes at room temperature. The reaction mixture is poured into cold water, neutralized to pH 5.5 with an aqueous solution of sodium bicarbonate. The organic layer is washed with water, dried over anhydrous sodium sulfate and the solvent is evaporated under reduced pressure. The residue is chromatographed on a column of silica gel [developing with ethylacetate-dichloromethane (1:1)] to give 2 g of benzhydryl 7-amino-3-(5-methyl-1,3,4-thiadiazol-2-yl)-3-cephem-4-carboxylate.

Melting point: 162°-164° C.(decomp.).

EXAMPLE 79

To a suspension of 0.443 g of the 7-amino-3-thiadiazole benzhydryl ester obtained in Example 78 in 2 ml of anisole is added 3 ml of trifluoroacetate acid under stirring and ice-cooling. After 30 minutes, the solvent is distilled off under reduced pressure. The residue is dissolved in 10% hydrochloric acid and the solution is neutralized with a saturated aqueous solution of sodium bicarbonate. The formed precipitates are filtered, and washed with water, acetone and then ether to give 0.21 g of 7-amino-3-(5-methyl-1,3,4-thiadiazol-2-yl)-3-cephem-4-carboxylic acid.

EXAMPLE 80

To a solution of 168 mg of diketen in 30 ml of dichloromethane is added dropwise 320 mg of bromine with stirring at $-40°$ C. The reaction mixture is added dropwise to a solution of 534 mg of the 7-amino-3-thiadiazole-4-carboxylic acid obtained in Example 79 and 363 mg of triethylamine in 6 ml of dichloromethane with stirring at $-40°$ C. After stirring for 15 minutes at room temperature, the reaction mixture is evaporated with reduced pressure. The residue is dissolved in 20 ml of acetone —H$_2$O (1:1), and to the solution is added 152 mg of thiourea in 10 ml of acetone. After two hours, the separated precipitates are collected by filtration, and washed with a small amount of acetone. The precipitates are dissolved in an aqueous solution of sodium bicarbonate, and the solution is charged on a column of Amberlite XAD-II and developed with water. The fractions containing the desired product are combined and lyophilized to give 300 mg of sodium 7-[(2-aminothiazol-4-yl)-acetamido]-3-(5-methyl-1,3,4-thiadiazol-2-yl)-3-cephem-4-carboxylate.

IR $\nu_{max}^{KBr}$ cm$^{-1}$: 1770($\beta$-lactam), 1620(carboxylate).
NMR(D$_2$O, ppm): 2.85(s,CH$_3$—), 3.73(s,—CH$_2$CO—), 3.94, 4.18 (ABq,C$_2$—H, J=18 Hz), 5.38(d,C$_6$—H, J=5 Hz), 5.86(d,C$_7$—H, J=5 Hz),

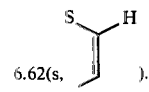
6.62(s, ).

EXAMPLE 81

To a solution of 3 g of benzhydryl 7-thienylacetamido-3-formyl-3-cephem-4-carboxylate in 20 ml of dimethylsulfoxide is added 0.88 g of thiobenzoylhydrazine. The reaction mixture is stirred for 4 hours, poured into cold water and shaken with ethyl acetate. The organic layer is washed with water, dried over sodium sulfate, and the solvent is evaporated in vacuo to give 3.8 g of the corresponding thiobenzoyl hydrazone.

IR $\nu_{max}^{KBr}$ cm$^{-1}$: 1790($\beta$-lactam), 1720(ester), 1670(amide).
NMR(CDCl$_3$, ppm): 3.56, 3.82(ABq,H=18 Hz, C$_2$—H), 3.81(s,—CH$_2$CO—), 4.92(d,J=5 Hz, C$_6$—H), 5.87(q,J=5 Hz, 9 Hz, C$_7$—H), 6.6(s,—CH=N—), 6.94(s,—CH$\phi_2$),

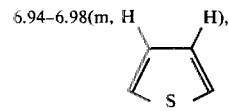
6.94-6.98(m, H H), 7.1-7.5(m,arom.),

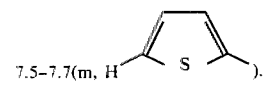
7.5-7.7(m, H ).

EXAMPLE 82

To a solution of 1 g of benzhydryl 7-thienylacetamido-3-thiobenzoylhydrazonomethyl-3-cephem-4-carboxylate in 10 ml of dioxane is added 0.28 g of DDQ, followed by stirring at room temperature for 30 minutes. The reaction mixture is filtered and the filtrate cake is washed with a small amount of dioxane. The combined filtrate is evaporated to dryness in vacuo and the residue recrystallized from ethyl acetate to give 0.6 g of benzhydryl 7-thienylacetamido-3-(5-phenyl-1,3,4-thiadiazol-2-yl)-3-cephem-4-carboxylate as pale yellow crystals.

Melting point; 226°–228° C.

IR $\nu_{max}^{KBr}$ cm$^{-1}$: 1790($\beta$-lactam), 1730(ester), 1670(amide).

NMR(DMSO-d$_6$, ppm); 3.81(s,—CH$_2$—), 3.97, 4.20(ABq,J=10 Hz, C$_2$—H$_2$), 5.35(d,J=5 Hz, C$_6$—H), 5.92(q,J=5 Hz, 9 Hz, C$_7$—H), 6.93(s,—CH$\phi_2$),

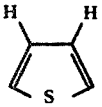
6.96–7.0(m, H   H ),

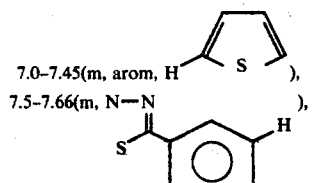
7.0–7.45(m, arom, H ),
7.5–7.66(m, N—N ),

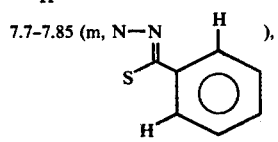
7.7–7.85 (m, N—N ), 9.28(d, 9 Hz, NH).

EXAMPLE 83

To a suspension of 300 mg of the 3-thiadiazole benzhydryl ester obtained in Example 82 in 1.5 ml of anisole is added 3 ml of trifluoroacetic acid under stirring at 0° C. After stirring for 20 minutes at room temperature, the reaction mixture is concentrated in vacuo. The residue is recrystallized from dry ether to give 213 mg. of 7-thienylacetamido-3-(5-phenyl-1,3,4-thiadiazol-2-yl)-3-cephem-4-carboxylic acid as pale yellow needles.

Melting point: 225°–227° C.

IR $\nu_{max}^{KBr}$ cm$^{-1}$: 1785($\beta$-lactam), 1660(—COOH).

NMR(DMSO-d$_6$, ppm): 3.95, 4.18(ABq,J=18 Hz, C$_2$—H$_2$), 4.5–5.0 (broad,s, COOH), 5.32(d,J=5 Hz, C$_6$—H), 5.86(q,J=5 Hz, 9 Hz, C$_7$—H,

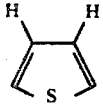
6.96–7.0 (m, H   H ),

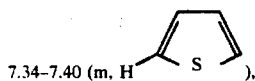
7.34–7.40 (m, H ),

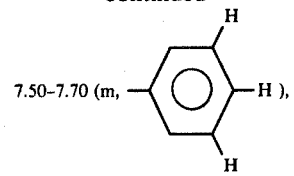
7.50–7.70 (m, H   H ),

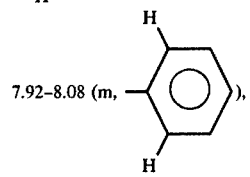
7.92–8.08 (m, ), 9.24(d,J=9 Hz, —CONH).

EXAMPLE 84

To a suspension of 1.56 g of pulverized phosphorous pentachloride in 12 ml of dry dichloromethane is added a solution of 1.19 g of pyridine in 12 ml of dichloromethane under stirring at −40° C. To the reaction mixture is added a solution of 1.67 g of the 3-thiadiazole benzhydryl ester obtained in Example 86 in 50 ml of dichloromethane at −40° C. After stirring for 1.5 hours at 0° C., to the reaction mixture is added 5 ml of n-butanol under stirring at −40° C. The resulting mixture is poured into water, and the solution is adjusted to pH 5.5 with sodium bicarbonate. The organic layer is washed with water, dried over anhydrous sodium sulfate and the solvent is evaporated under reduced pressure. The residue is chromatographed on a column of silica gel [developing an ethylacetate-dichloromethane (1:1)] to give 0.75 g of benzhydryl 7-amino-3-(5-phenyl-1,3,4-thiadiazol-2-yl)-3-cephem-4-carboxylate.

IR $\nu_{max}^{KBr}$ cm$^{-1}$: 1780($\beta$-lactam), 1730(ester).

NMR(DMSO-d$_6$, ppm): 3.27(broad s,—NH$_2$), 3.88, 4.13(ABq, J=18 Hz, C$_2$—H), 4.99(d,J=5 Hz, C$_6$—H), 5.22(d,J=5 Hz, C$_7$—H), 6.89(s,—CH—$\phi_2$), 7–7.9(m,arom.).

EXAMPLE 85

To a solution of 0.263 g of benzhydryl 7-amino-3-(5-phenyl-1,3,4-thiadiazol-2-yl)-3-cephem-4-carboxylate (obtained in Example 84) in 5 ml of anhydrous dichloromethane is dropwise added 0.171 g of $\omega$-bromoacetoacetyl bromide and then 0.0396 g of pyridine under stirring for 30 minutes at −40° C. The reaction mixture is poured into cold water. The dichloromethane layer is separated, washed with water, dried over anhydrous sodium sulfate and the solvent is evaporated in vacuo. To a solution of the residue is 2 ml of DMA is added 0.038 g of thiourea, followed by stirring for 40 minutes at room temperature. The reaction mixture is poured into water, shaken with ethyl acetate and the organic layer is washed with water, dried over anhydrous sodium sulfate. After removal of the solvent under reduced pressure, the residue is chromatographed on a column of silica gel [eluting with ethyl acetate-benzene (1:1)] to give 0.158 g of benzhydryl 7-[2-(2-aminothiazol-4-yl)acetamido)-3-(5-phenyl-1,3,4-thiadiazol-2-yl)-3-cephem-4-carboxylate as pale yellow crystals.

Melting point: 160°–164° C.

IR $\nu_{max}^{KBr}$ cm$^{-1}$: 1785($\beta$-lactam), 1725(ester).

NMR(DMSO-d$_6$, ppm): 3.44(s,—CH$_2$—), 3.98, 4.21(ABq,C$_2$—H J=18 Hz), 5.34(d,C$_6$—H J=5 Hz), 5.94(q,C$_7$—H J=5, 9 Hz),

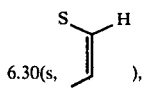

6.93(s,—CHφ₂), 7.0–7.9(m,aromatic H), 9.94(d,NH J=9 Hz).

EXAMPLE 86

A mixture of 0.12 g of the 3-thiadiazole benzhydryl ester obtained in Example 85, 1 ml of anisole and 2 ml of trifluoroacetic acid is stirred for 30 minutes at room temperature. After removal of the solvent under reduced pressure, the residue is triturated with the addition of absolute ether. The precipitates are filtered, washed with ether. 0.09 g of 7-[(2-aminothiazol-4-yl)-acetamido]-3-(5-phenyl-1,3,4-thiadiazol-2-yl)-3-cephem-4-carboxylic acid.

IR $\nu_{max}^{KB\gamma}$ cm⁻¹: 1785(β-lactam), 1620(carboxylate).

NMR(DMSO-d₆, ppm): 3.45(s,—CH₂—), 3.94, 4.18(ABq,C₂—H J=18 Hz), 5.30(d,C₆—H J=5 Hz), 5.86(q,C₇—H J=5,9 Hz),

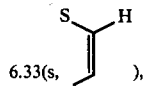

7.4–8.1(m,aromatic H).

EXAMPLE 87

To a solution of 6.5 g of benzhydryl 7-thienylacetamido-3-formyl-3-cephem-4-carboxylate in 20 ml of dimethylsulfoxide is added 1.4 g of 4-methylthiosemicarbazide. The mixture is stirred for 30 minutes at room temperature, poured into cold water and shaken with ethyl acetate. The organic layer is washed with water, dried over anhydrous sodium sulfate, and the solvent is evaporated. The residue is chromatographed on a column of silica gel [eluting with benzene-ethyl acetate(3:1)] to give 5.5 g of the corresponding 4-methylthiosemicarbazone.

IR $\nu_{max}^{KB\gamma}$ cm⁻¹: 1785 (β-lactam), 1720 (ester), 1678(amide).

UV$\lambda_{max}^{EtOH}$ nm(ε): 350(31,100).

NMR(DMSO-d₆, ppm); 2.98(d,N—CH₃ J=5 Hz), 3.75(s,—CH₂—) 3.57, 4.53(ABq,C₂—H J=18 Hz), 5.21(d,C₆—H J=4 Hz), 5.79(q,C₇—H J=4,8 Hz), 6.87(s,—CHφ₂), 8.24(s,—CH=N—), 8.45 (d,—NH J=5 Hz), 9.17(d,NH J=8 Hz), 7.1–7.7(m,aromatic H), 11.7(s,NH).

EXAMPLE 88

To a solution of 1 g of benzhydryl 7-thienylacetamido-3-formyl-3-cephem-4-carboxylate in 5 ml of dimethylsulfoxide is added 0.362 g of 4-benzyl-thiosemicarbazide. The mixture is allowed to react at room temperature for 2.5 hours. After working up as described in Example 87, the obtained crude product is chromatographed on a column of silica gel [eluting with benzene-ethyl acetate (7:1)] to give 0.6 g of the corresponding 4-benzylthiosemicarbazone.

IR $\nu_{max}^{KBr}$ cm⁻¹: 1792(β-lactam), 1723(ester), 1680(amide).

NMR(CDCl₃, ppm): 3.33, 3.84(ABq,C₂—H J=18 Hz), 3.79(s,—CH₂—), 4.88(d,C₆—H J=5 Hz), 4.96(d,—CH₂φ J=4 Hz), 5.86(q,C₇—H J=5,9 Hz), 6.53(d,NH J=9 Hz), 6.95(s,—CHφ₂), 7.3–7.5(m,aromatic H), 7.89(s,—CH=N—), 9.12(br.s,NH).

EXAMPLE 89

A solution of 4.5 g of the 4-methylthiosemicarbazone (obtained in Example 93) in 30 ml of acetic anhydride and 30 ml of acetic acid is stirred at 80° C. for 3 hours under a stream of nitrogen. Excess acetic anhydride and acetic acid are distilled off under reduced pressure and the resulting product is a mixture of monoacetyl and diacetyl derivatives. The mixture is chromatographed on a column of silica gel [eluting with benzene-ethyl acetate(1:1)] to give 2.0 g of monoacetyl derivative (a 3:1 mixture of two isomers) and 1.6 g of diacetyl derivative.

Monoacetyl derivative (A):

NMR(CDCl₃, ppm): 2.20(s,CH₃), 2.84(d,N—CH₃ J=5 Hz), 3.81(s,—CH₂—), 4.89(d,C₆—H J=5 Hz), 5.85(q,C₇—H J=5,8 Hz), 6.64(d,NH J=8 Hz), 8.26(s,—CN=N—).

Monoacetyl derivative (B):

NMR(CDCl₃, ppm): 2.22(s,CH₃), 3.04(d,N=CH₃ J=5 Hz), 4.99(d,C₆—H J=5 Hz), 3.79(s,—CH₂—), 5.76(q,C₇—H J=5,8 Hz).

Diacetyl derivative:

IR $\nu_{max}^{KBr}$ cm⁻¹: 1780(β-lactam), 1712 (ester).

NMR(CDCl₃, ppm): 2.25(s,CH₃), 3.33(C₂—H, NCH₃), 3.79(s,—CH₂—), 4.91(d,C₆—H J=5 Hz), 5.81(q,C₇—H J=5,8 Hz), 6.73(d,NH J=8 Hz), 6.96(s,—CHφ₂).

EXAMPLE 90

(1) Ring closure of the monoacetyl derivative

One gram of the 3-monoacetylthiosemicarbazone derivative (3:1 mixture of two isomers) obtained in Example 89 is dissolved in 10 ml of anhydrous dioxane and to the solution is added 0.53 g of DDQ, followed by stirring at 45° C. for 12 hours.

After cooling, the reaction mixture is filtered and the filter cake is washed with a small amount of dioxane. The combined filter is evaporated to dryness under reduced pressure and the residue is chromatographed on a column of silica gel [eluting with ethyl acetate-dichloromethane (1:2)] to give 0.45 g of benzhydryl 7-thienylacetamido-3-(5-N-acetyl-N-methylamino-1,3,4-thiadiazol-2-yl)-3-cephem-4-carboxylate (Compound A) and 0.15 g of benzhydryl 7-thienylacetamido-3-(5-methylamino-1,3,4-thiadiazol-2-yl)-3-cephem-4-carboxylate (Compound B).

Compound A (colourless cubics)

Melting point: 130°–3° C.

IR $\nu_{max}^{KBr}$ cm⁻¹: 1783(β-lactam), 1725(ester), 1663(amide).

NMR(DMSO-d₆, ppm); 2.79(s,CH₃), 3.79(s,—CH₂—), 3.83, 4.03 (ABq,C₂—H J=18 Hz), 5.26(d,C₆—H J=5 Hz), 5.84(q,C₇—H J=5,8 Hz), 6.85(s,—CHφ₂), 6.9–7.4(m,aromatic H), 9.20(d,NH J=8 Hz).

Compound B (colourless plates)

Melting point: 205°–208° C.

IR $\nu_{max}^{KBr}$ cm⁻¹: 1782(β-lactam), 1738(ester).

NMR(DMSO-d₆, ppm); 2.39(s,COCH₃), 3.54(s,CH₃), 3.79(s,—CH₂—), 3.86, 4.08(ABq,C₂—H J=18 Hz), 5.28(d,C₆—H J=5 Hz), 5.88 (q,C₇—H J=5,8 Hz), 6.80(s,—CHφ₂), 6.9–7.4(aromatic H). 9.23(d,NH J=8 Hz).

(2) Ring closure of the diacetyl derivative.

A mixture of 0.8 g of the 3-diacetylthiosemicarbazone derivative obtained in Example 84 and 0.4 g of DDQ in 10 ml of dioxane is stirred for one hour at 80° C.

After working up as described above, the crude product is chromatographed on a column of silica gel [eluting with benzene-ethyl acetate (1:1)] to give 0.56 g of the 3-thiadiazole derivative [Compound A].

EXAMPLE 91

A solution of 0.6 g of the 4-benzylthiosemicarbazone obtained in Example 88 in 6 ml of acetic anhydride and 6 ml of acetic acid is stirred at 70° C. for 8 hours. Excess acetic anhydride and acetic acid are distilled off under reduced pressure. The residue is chromatographed on a column of silica gel [eluting with benzene-ethyl acetate (3:1)] to give a mixture of two monoacetylthiosemicarbazone isomers (0.5 g).

IR $\nu_{max}^{KBr}$ cm$^{-1}$: 1790($\beta$-lactam), 1720(ester), 1665(amide), 1610(acetyl).

EXAMPLE 92

A mixture of 0.1 g of the monoacetylthiosemicarbazone derivative obtained in Example 91 and 0.05 g of DDQ in 3 ml of dioxane is stirred at 70° C. for 8 hours. After working up as described in Example 96, the crude product is chromatographed on a column of silica gel [eluting with benzene-ethyl acetate (3:1)] to give 0.035 g of benzhydryl 7-thienylacetamido-3-(5-N-acetyl-N-benzylamino-1,3,5-thiadiazol-2-yl)-3-cephem-4-carboxylate and 0.021 g of benzhydryl 7-thienylacetamido-3-(5-benzylamino-1,3,4-thiadiazol-2-yl)-3-cephem-4-carboxylate.

N-acetyl-N-benzylaminothiadiazole derivative (the former).

IR $\nu_{max}^{KBr}$ cm$^{-1}$: 1793($\beta$-lactam), 1730(ester), 1690(amide).

NMR(DMSO-d$_6$, ppm): 2.36(s,COCH$_3$), 3.80(s,—CH$_2$—), 4.12, 3.88 (ABq,C$_2$—H J=18 Hz), 5.28(d,C$_6$—H J=5 Hz), 5.89(q,C$_7$—H J=5,8 Hz), 6.83(s,—CH$\phi_2$), 5.37(s,—CH$_2\phi$), 6.9-7.5 (m,aromatic H), 9.24(d,NH J=8 Hz).

benzylaminothiadiazole derivative (the latter)

IR $\nu_{max}^{KBr}$ cm$^{-1}$: 1783($\beta$-lactam), 1725(ester), 1670(amide).

NMR(DMSO-d$_6$, ppm): 3.79(s,—CH$_2$—), 4.40(s,—CH$_2\phi$), 4.03, 3.82(ABq,C$_2$—H J=18 Hz), 5.25(d,C$_6$—H J=5 Hz), 5.83(q,C$_7$—H J=5,9 Hz), 6.84(s,—CH$\phi_2$), 6.9-7.5(m,aromatic H), 9.22(d,NH J=9 Hz).

EXAMPLE 93

A mixture of 0.5 g of the benzhydrylester (Compound A) obtained in Example 90, 2 ml of anisole and 4 ml of trifluoroacetic acid is stirred for 20 minutes at room temperature.

After removal of the solvent under reduced pressure, the residue is triturated with the addition of absolute ethyl ether. The precipitates are collected by filtration to afford 0.3 g of the corresponding carboxylic acid trifluoroacetic acid salt. The salt is dissolved in an aqueous solution of sodium bicarbonate, and the solution is charged on a column of Amberlite XAD-II and developed with water and then 5% ethanol. The fractions containing the desired product are combined and lyophilized to give 0.075 g of sodium 7-thienylacetamido-3-(5-N-acetyl-N-methylamino-1,3,4-thiadiazol-2-yl)-3-cephem-4-carboxylate.

IR $\nu_{max}^{KBr}$ cm$^{-1}$: 1778($\beta$-lactam), 1663(amide), 1615(carboxylate).

NMR(DMSO-d$_6$, ppm): 2.86(s,COCH$_3$), 3.66(s,CH$_3$), 3.78(s,—CH$_2$—), 4.14(ABq,C$_2$—H J=18 Hz), 5.12(d,C$_6$—H J=5 Hz), 5.58(q,C$_7$—H J=5,9 Hz), 6.8-7.4(m,aromatic H), 9.10 (d,NH J=9 Hz).

EXAMPLE 94

0.4 g of the benzhydrylester (Compound B) obtained in Example 90 is treated with 2 ml of anisole and 4 ml of trifluoroacetic acid in the manner described in Example 93. 0.2 g of 7-thienylacetamido-3-(5-methyl-1,3,4-thiadiazol-2-yl)-3-cephem-4-carboxylic acid (trifluoroacetic acid salt) is given.

IR $\nu_{max}^{KBr}$ cm$^{-1}$: 1780($\beta$-lactam).

EXAMPLE 95

The N-acetyl-N-benzylaminothiadiazole derivative obtained in Example 92, 0.5 is treated with 2 ml of anisole and 3 ml of trifluoroacetic acid in the manner described in Example 93.

0.22 g of 7-thienylacetamido-3-(5-N-acetyl-N-benzylamino-1,3,4-thiadiazol-2-yl)-3-cephem-4-carboxylic acid (trifluoroacetic acid salt) is obtained.

IR $\nu_{max}^{KBr}$ cm$^{-1}$: 1790($\beta$-lactam), 1680(amide).

EXAMPLE 96

The benzylaminothiadiazole derivative obtained in Example 92, 0.35 g is treated with 1.5 ml of anisole and 2.5 ml of trifluoroacetic acid in the manner described in Example 93.

0.15 g of 7-thienylacetamido-3-(5-benzylamino-1,3,4-thiadiazol-2-yl)-3-cephem-4-carboxylic acid (trifluoroacetic acid salt) is obtained.

IR $\nu_{max}^{KBr}$ cm$^{-1}$: 1782($\beta$-lactam), 1680(amide).

EXAMPLE 97

To a suspension of 0.824 g of phosphorus pentachloride in 6 ml of anhydrous dichloromethane is added 0.625 g of anhydrous pyridine in 6 ml of anhydrous dichloromethane at −55° C. with stirring. To the mixture is added 0.850 g of the N-acetyl-N-methylamino derivative (Compound A) obtained in Example 96 with stirring at −50° C. and stirring is continued at 0°-3° C. for an additional hour. To the mixture is added 2 ml of n-butanol at 50° C. and the mixture is stirred for 30 minutes at 0° C. The reaction mixture is poured into cold water. After neutralization with sodium bicarbonate, the mixture is extracted with ethyl acetate. The organic layer is washed with a saturated aqueous solution of sodium chloride, dried over anhydrous sodium sulfate, and the solvent is evaporated under reduced pressure. The residue is chromatographed on a column of silica gel [eluting with ethyl acetate-dichloromethane (1:1)] to give 0.298 g of 7-amino-3-(5-N-acetyl-N-methylamino-1,3,4-thiadiazol-2-yl)-3-cephem-4-carboxylic acid benzhydryl ester.

IR $\nu_{max}^{KBr}$ cm$^{-1}$: 1785($\beta$-lactam), 1732(ester).

NMR(CDCl$_3$, ppm): 1.8(br.s,NH$_2$), 2.36(s,COCH$_3$), 3.60(s,CH$_3$), 3.70, 4.05(ABq,C$_2$—H J=18 Hz), 4.85(d,C$_6$—H J=5 Hz), 5.04(d,C$_7$—H J=5 Hz), 7.18(s,aromatic H), 7.92(s,—CH$\phi_2$).

EXAMPLE 98

To a solution of diketene (62.7 mg) dissolved in 1.5 ml of dichloromethane, bromine (120 mg) in 1 ml of dichloromethane is added dropwise with stirring at −50° C. Stirring and cooling are maintained for 15 minutes. The reaction mixture is added dropwise to a solution of 0.260 g of benzhydryl 7-amino-3-(5-N-acetyl-N-methylamino-1,3,4-thiadiazol-2-yl)-3-cephem-4-carboxylate obtained in Example 97 and 0.04 g of pyridine in 3 ml of dichloromethane with stirring at −30° C. After 30 minutes, the reaction mixture is washed with an aqueous solution of sodium chloride. The organic layer is evaporated under reduced pressure and the residue is dissolved in 3 ml of DMA. To the solution is added 0.04 g of thiourea and the solution is allowed to react at room temperature for 1.5 hours. The reaction mixture is poured into ice water. The organic layer is washed with water, dried over anhydrous sodium sulfate and evaporated to dryness. The residue is chromatographed on a column of silica gel [eluting with ethyl acetate] to give 0.135 g of benzhydryl 7-[2-(2-aminothiazol-4-yl)acetamido]-3-(5-N-acetyl-N-methylamino-1,3,4-thiadiazol-2-yl)-3-cephem-4-carboxylate.

IR $\nu_{max}^{KBr}$ cm$^{-1}$: 1785($\beta$-lactam), 1730(ester), 1675(amide).

NMR(DMSO-d$_6$, ppm): 2.39(s,COCH$_3$), 3.42(s,—CH$_2$—), 3.54(s,CH$_3$), 3.86, 4.08(ABq,C$_2$—H J=18 Hz), 5.29(d,C$_6$—H J=5 Hz), 5.84(q,C$_7$—H J=5,9 Hz),

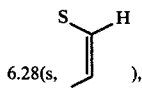

6.28(s, ), 6.79(s,—CH$\phi_2$), 7.29(s,aromatic H), 9.00(d,NH J=9 Hz).

EXAMPLE 99

A mixture of 0.075 g of the benzhydryl ester obtained in Example 98, 1 ml of anisole and 2 ml of trifluoroacetic acid is stirred for 30 minutes at room temperature. After removal of the solvent under reduced pressure, the residue is triturated with the addition of absolute ether. The precipitates are dissolved in an aqueous solution of sodium bicarbonate, and the solution is chromatographed on a column of Amberlite XAD-II using water and then 5% ethanol as eluent. The fractions containing the active product are combined and lyophilized to give 0.035 g of sodium 7-[2-(2-aminothiazol-4-yl)acetamido]-3-(5-N-acetyl-N-methylamino-1,3,4-thiadiazol-2-yl)-3-cephem-4-carboxylate.

IR $\nu_{max}^{KBr}$ cm$^{-1}$: 1765($\beta$-lactam), 1685(amide), 1610(carboxylate).

NMR(D$_2$O, ppm); 2.55(s,—COCH$_3$), 3.69(s,—CH$_2$—), 3.79 (s,CH$_3$), 3.91, 4.17(ABq,C$_2$—H J=18 Hz), 5.38(d,C$_6$—H J=5 Hz), 5.86(d,C$_7$—H J=5 Hz),

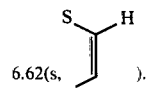

6.62(s, ).

| Strain of microorganism | Antibacterial spectra (mcg/ml, agar dilution method) | |
|---|---|---|
| | Product of this Example | Cefazolin |
| S. aureus 209P | 0.39 | ≦0.2 |
| E. coli NIHJ | 0.39 | 1.5 |
| E. coli 0-111 | ≦0.2 | 0.78 |
| E. coli T-7 | 6.25 | 25 |
| K. pneumoniae DT | ≦0.2 | 1.56 |
| K. pneumoniae GN3835 | 0.78 | 1.56 |
| P. vulgaris IF03988 | 0.23 | 3.13 |
| P. mirabilis GN43459 | ≦0.2 | 3.13 |
| P. morganii IF03168 | 1.56 | 25 |
| P. rettgeri 8(TNO.336) | ≦0.2 | ≦0.2 |
| P. rettgeri GN4733 | ≦0.2 | 25 |
| Ent. cloacae IFO 12937 | 1.56 | >100 |
| Cit. freundii GN99 | 1.56 | 12.5 |
| Cit. freundii GN1706 | 1.56 | >100 |

EXAMPLE 100

A solution of 3.1 g of the thiosemicarbazone benzhydryl ester (obtained in Example 21) and 1.3 g of chloranil in 30 ml of dioxane is stirred for 11 hours at room temperature. After working up as described in Example 23, 2.4 g of benzhydryl 7-thienylacetamido-3-(5-dimethylamino-1,3,4-thiadiazole-2-yl)-3-cephem-4-carboxylate is obtained.

Melting point: 189°–191° C. (pale yellow plates).

EXAMPLE 101

A solution of 2.4 g of the thiosemicarbazone carboxylic acid (obtained in Example 41) and 1.3 g of chloranil in 21 ml of dioxane is stirred for 13 hours at room temperature. After working up as described in Example 42, 1.6 g of the corresponding thiadiazole derivative is obtained.

Melting point: 171.5°–173° C. (decomp.).

EXAMPLE 102

A solution of 3.4 g of the diacetate (obtained in Example 17) and 1.3 g of chloranil in 21 ml of dioxane is stirred for 18 hours at 42° C. After working up as described in Example 18, 2.75 g of the corresponding thiadiazole derivative is obtained.

EXAMPLE 103

A solution of 2.1 g of the thiosemicarbazone (obtained in Example 71) and 0.9 g of chloranil in 15 ml of dioxane is stirred for 12 hours at room temperature. After working up as described in Example 72, 1.4 g of the corresponding thiadiazole derivative is obtained.

What we claim is:

1. A member of the group consisting of a compound of the formula

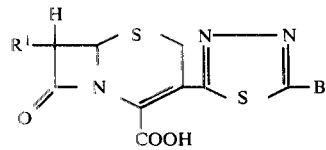

and a pharmaceutically acceptable salt thereof, wherein R$^1$ represents 2-thienylacetamido or 2-(2-iminothiazolin-4-yl)-acetamido and B represents lower alkyl, phenyl, methylamino, dimethylamino, N-methyl-N-acetylamino or acetylamino.

2. A compound as in claim 1, wherein $R^1$ represents 2-(2-imino-thiazolin-4-yl)acetamido.

3. A compound as in claim 1, wherein B is methyl.

4. A compound as in claim 1, wherein B is acetylamino, dimethylamino or N-acetyl-N-methylamino.

5. A compound as in claim 1, said compound being 3-(5-acetylamino-1,3,4-thiadiazol-2-yl)-7-[2-(2-imino-thiazolin-4-yl)acetamido]-3-cephem-4-carboxylic acid.

6. A compound as in claim 1, said compound being 3-(5-dimethylamino-1,3,4-thiadiazol-2-yl)-7-[2-(imino-thiazolin-4-yl)acetamido]-3-cephem-4-carboxylic acid.

7. A compound as in claim 1, said compound being 3-(5-N-acetyl-N-methylamino-1,3,4-thiadiazol-2-yl)-7-]2-(2-iminothiazolin-4-yl)acetamido]-3-cephem-4-carboxylic acid.

8. A compound as in claim 1, wherein the carboxylic gropu at the 4-position is in the form of the sodium salt.

* * * * *